(12) United States Patent
Newberry

(10) Patent No.: US 9,642,538 B2
(45) Date of Patent: May 9, 2017

(54) SYSTEM AND METHOD FOR A BIOSENSOR MONITORING AND TRACKING BAND

(71) Applicant: Sanmina Corporation, San Jose, CA (US)

(72) Inventor: Robert Steven Newberry, New Hope, AL (US)

(73) Assignee: Sanmina Corporation, San Jose, CA (US)

( * ) Notice: Subject to any disclaimer, the term of this patent is extended or adjusted under 35 U.S.C. 154(b) by 0 days.

(21) Appl. No.: 15/275,444

(22) Filed: Sep. 25, 2016

(65) Prior Publication Data

US 2017/0014035 A1    Jan. 19, 2017

Related U.S. Application Data

(63) Continuation-in-part of application No. 14/866,500, filed on Sep. 25, 2015, and a continuation-in-part of application No. 12/275,388, filed on Sep. 24, 2016.
(Continued)

(51) Int. Cl.
*A61B 5/1455* (2006.01)
*A61B 5/0205* (2006.01)
(Continued)

(52) U.S. Cl.
CPC ........ *A61B 5/02055* (2013.01); *A61B 5/0002* (2013.01); *A61B 5/0008* (2013.01);
(Continued)

(58) Field of Classification Search
None
See application file for complete search history.

(56) References Cited

U.S. PATENT DOCUMENTS

| 4,913,150 A | 4/1990 | Cheung et al. |
| 6,985,763 B2 | 1/2006 | Boas et al. |

(Continued)

OTHER PUBLICATIONS

PCT/US2016/053532. Int'l Search Report & Written Opinion (Dec. 9, 2016).

(Continued)

*Primary Examiner* — Eric Winakur
*Assistant Examiner* — Marjan Fardanesh
(74) *Attorney, Agent, or Firm* — Loza & Loza LLP; Julio M. Loza; Jessica W. Smith

(57) ABSTRACT

A health care band operably attaches a biosensor to a patient. The biosensor includes one or more sensors for collecting vitals of a patient and a wireless transmitter that is configured to communicate with an EMR network that stores and maintains an EMR of the patient. The biosensor stores a unique identification associated with the patient's EMR such that vitals measured by the biosensor may be transmitted with the patient's unique identification for storage in the patient's EMR. The sensors in the biosensor may include a thermometer, motion detector/accelerometer, pulse detector and oximeter, etc. In an embodiment, one of the sensors in the biosensor includes a photoplethysmography (PPG) based sensor that may be configured to continuously or periodically measure a patient's vitals, such as heart rate, pulse, blood oxygen levels, blood glucose or insulin levels, or other blood analytics in vitro.

20 Claims, 28 Drawing Sheets

Related U.S. Application Data

(60) Provisional application No. 62/194,264, filed on Jul. 19, 2015, provisional application No. 62/276,934, filed on Jan. 10, 2016, provisional application No. 62/307,375, filed on Mar. 11, 2016, provisional application No. 62/312,614, filed on Mar. 24, 2016, provisional application No. 62/373,283, filed on Aug. 10, 2016, provisional application No. 62/383,313, filed on Sep. 2, 2016.

(51) Int. Cl.

| | | |
|---|---|---|
| *A61B 90/96* | (2016.01) | |
| *A61B 5/117* | (2016.01) | |
| *A61B 5/00* | (2006.01) | |
| *G06F 19/00* | (2011.01) | |
| *A61B 5/024* | (2006.01) | |
| *A61B 5/145* | (2006.01) | |
| *A61B 5/11* | (2006.01) | |
| *A61B 5/021* | (2006.01) | |

(52) U.S. Cl.
CPC ............ *A61B 5/117* (2013.01); *A61B 5/6825* (2013.01); *A61B 90/96* (2016.02); *G06F 19/3406* (2013.01); *A61B 5/021* (2013.01); *A61B 5/02416* (2013.01); *A61B 5/02438* (2013.01); *A61B 5/1118* (2013.01); *A61B 5/14532* (2013.01); *A61B 5/14546* (2013.01); *A61B 5/14551* (2013.01)

(56) References Cited

U.S. PATENT DOCUMENTS

| | | | |
|---|---|---|---|
| 9,149,216 B2 | 10/2015 | Eisen et al. | |
| 2003/0229276 A1* | 12/2003 | Sarussi | A61B 5/02433 600/322 |
| 2008/0208019 A1 | 8/2008 | Nitzan | |
| 2011/0224518 A1* | 9/2011 | Tindi | A61B 5/14552 600/323 |
| 2011/0275978 A1* | 11/2011 | Hyde | A61K 33/00 604/20 |
| 2012/0238844 A1 | 9/2012 | Grata | |
| 2013/0110311 A1 | 5/2013 | Steeg et al. | |
| 2013/0310669 A1 | 11/2013 | Meir Nitzan | |
| 2014/0046160 A1 | 2/2014 | Terashima et al. | |
| 2014/0112940 A1 | 4/2014 | Lane | |
| 2014/0275852 A1 | 9/2014 | Hong et al. | |
| 2014/0297313 A1 | 10/2014 | Condurso et al. | |
| 2015/0088007 A1 | 3/2015 | Bardy et al. | |
| 2015/0094914 A1 | 4/2015 | Abreu | |
| 2015/0109617 A1 | 4/2015 | Gilbert et al. | |
| 2015/0148635 A1 | 5/2015 | Benaron | |
| 2015/0150453 A1 | 6/2015 | Abreu | |
| 2015/0182172 A1 | 7/2015 | Shelley et al. | |
| 2015/0282747 A1 | 10/2015 | Thiele | |
| 2015/0366471 A1 | 12/2015 | LeBoeuf et al. | |
| 2016/0018257 A1 | 1/2016 | Mirov et al. | |
| 2016/0058347 A1 | 3/2016 | Reichgott et al. | |
| 2016/0066863 A1 | 3/2016 | Thaveeprungsriporn et al. | |
| 2016/0100781 A1 | 4/2016 | Bechtel et al. | |

OTHER PUBLICATIONS

KC Manhesh et al., Wearable Wireless Intelligent Multi-Parameter Health Monitoring Watch, 2013, Texas Instruments India Educators' Conference, IEEE, p. 61-64.

Abdallah et al., Design of a Compact Multi-Sensor System for Non-Invasive Glucose Monitoring Using Optical Spectroscopy, International Conference on Electronics, Biomedical Engineering and its Applications (ICEBEA'2012), Jan. 7-8, 2012, p. 310-317.

Forst et al., Cardiovascular Effects of Disturbed Insulin Activity in Metabolic Syndrome and in Type 2 Diabetic Patients, Insulin Secretion and Action, Horm Metab Res; 2009, 41; p. 123-131.

Mohamed Elgendi, On the Analysis of Fingertip Photoplethysmogram Signals, Current Cardiology Reviews, 2012, 8, p. 14-25, Bentham Science Publishers.

Wikipedia, Cytochrome P450, Dec. 31, 2015, p. 1-12.

Oliver Wieben, Light Absorbance in Pulse Oximetry, Taylor & Francis, 1997, IOP Publishing, p. 1-20.

Wikipedia, Photoplethysmogram, Jul. 25, 2015, p. 1-4.

\* cited by examiner

SYSTEM AND METHOD FOR A BIOSENSOR MONITORING AND TRACKING BAND

CROSS REFERENCE TO RELATED APPLICATIONS

The present application claims priority under 35 U.S.C. §119 to U.S. Provisional Application No. 62/194,264 entitled, "System and Method for Glucose Monitoring," filed Jul. 19, 2015, and hereby expressly incorporated by reference herein. The present application claims priority as a continuation in part under 35 U.S.C. §120 to U.S. Utility application Ser. No. 14/866,500 entitled, "System and Method for Glucose Monitoring," filed Sep. 25, 2015, and hereby expressly incorporated by reference herein. The present application claims priority under 35 U.S.C. §119 to U.S. Provisional Application No. 62/276,934 entitled, "System and Method for Health Monitoring including a Remote Device," filed Jan. 10, 2016, and hereby expressly incorporated by reference herein. The present application claims priority under 35 U.S.C. §119 to U.S. Provisional Application No. 62/307,375 entitled, "System and Method for Health Monitoring using a Non-Invasive, Multi-Band Sensor," filed Mar. 11, 2016, and hereby expressly incorporated by reference herein. The present application claims priority under 35 U.S.C. §119 to U.S. Provisional Application No. 62/312,614 entitled, "System and Method for Determining Biosensor Data using a Broad Spectrum Light Source," filed Mar. 24, 2016, and hereby expressly incorporated by reference herein. The present application claims priority under 35 U.S.C. §119 to U.S. Provisional Application No. 62/373,283 entitled, "System and Method for a Biosensor Monitoring and Tracking Band," filed Aug. 10, 2016, and hereby expressly incorporated by reference herein. The present application claims priority under 35 U.S.C. §119 to U.S. Provisional Application No. 62/383,313 entitled, "System and Method for a Drug Delivery and Biosensor Patch," filed Sep. 2, 2016, and hereby expressly incorporated by reference herein. The present application claims priority as a continuation in part under 35 U.S.C. §120 to U.S. Utility application Ser. No. 15/275,388 entitled, "System And Method For Health Monitoring Using A Non-Invasive, Multi-Band Biosensor," filed Sep. 24, 2016, and hereby expressly incorporated by reference herein.

FIELD

This application relates to a systems and methods of non-invasive, autonomous health monitoring band, and in particular a health monitoring band that assists in tracking patient's medical records for use in an electronic medical record system and network.

BACKGROUND

Tracking of a patient's admission, medical records, and/or administration of medicine and treatments to the patient in a hospital or other healthcare facility currently includes use of a barcode on an armband of the patient. The bar code on the patient's armband must be scanned with a physical scanner to identify the patient prior to administering the medicine, recording vitals, performing procedures, etc.

In addition, the patient's vitals, such as temperature, blood oxygen levels, blood pressure, etc., must be monitored periodically typically using one or more additional instruments. For example, additional instruments for obtaining vitals of a patient include blood pressure cuffs, thermometers, SO2 measurement devices, glucose level meters, etc. Often, multiple instruments must be brought to a patient's room by a caretaker and the measurements collected by each instrument. This monitoring process can be time consuming, inconvenient and is not always continuous. It may also disrupt sleep of the patient. The measurements of the vitals must then be manually recorded into the patient's electronic medical record.

In addition, detection of substances and measurement of concentration level or indicators of various substances in a patient's blood vessels is important in health monitoring. Currently, detection of concentration levels of blood substances is performed by drawing blood from a blood vessel using a needle and syringe. The blood sample is then transported to a lab for analysis. This type of monitoring is invasive, non-continuous and time consuming.

One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood. Such PPG techniques are heretofore been limited to determining oxygen saturation.

As such, there is a need for a patient monitoring system that includes a continuous and non-invasive biosensor that measures patient vitals and monitors concentration levels or indicators of one or more substances in blood flow.

SUMMARY

According to a first aspect, a health care monitoring system includes a health care band configured for attachment to a patient and a biosensor attached to the health care band. The biosensor includes a memory configured to store a unique patient identification, a temperature sensor configured to obtain a temperature of the patient, a PPG circuit and a processing circuit. The PPG circuit is configured to emit light at a plurality of wavelengths directed at skin of the patient and obtain a plurality of spectral responses at each of the plurality of wavelengths of light reflected from the skin. The processing circuit is configured to process the spectral responses at the plurality of wavelengths, determine patient vitals using the spectral responses, wherein the patient vitals include oxygen saturation levels, and obtain concentration levels of one or more additional substances in arterial blood flow using the spectral responses. The health care monitoring circuit further includes a wireless transceiver configured to transmit the temperature, oxygen saturation levels, the concentration levels of the one or more additional substances and the unique patient identification.

According to a second aspect, a biosensor is configured for attachment to a patient and includes a memory configured to store a unique patient identification, a temperature sensor configured to obtain a temperature of the patient, and a PPG circuit. The PPG circuit is configured to generate at least a first spectral response for light reflected around a first wavelength from skin tissue of the patient, generate at least a second spectral response for light detected around a second wavelength reflected from the skin tissue of the patient. The biosensor further includes a processing circuit configured to process the first and second spectral responses at the first wavelength and the second wavelength, determine patient vitals using the first and second spectral responses, wherein the patient vitals include oxygen saturation levels, and obtain concentration levels of one or more additional substances in arterial blood flow using the first and second spectral responses. The biosensor further includes a wireless transceiver configured to transmit the temperature, oxygen saturation levels, the concentration levels of the one or more additional substances and the unique patient identification.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Figure 1A:
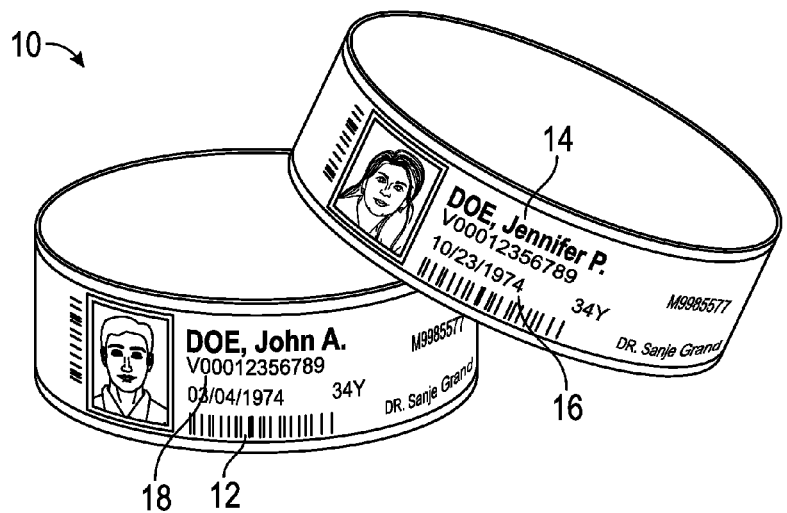
FIG. 1A illustrates a perspective view of an embodiment of a known arm band for tracking of a patient.

FIG. 1A illustrates a perspective view of an embodiment of a known arm band 10 for tracking of a patient. The arm band 10 includes a barcode 12 that is printed with a unique patient identification 18. The arm band may include other patient information such as a patient name 14 and date of birth 16. A hospital or other health care facility associates the unique patient identification with a patient and uses the patient identification to identify an electronic medical record (EMR), also known as an electronic health record (EHR), for the patient and for tracking administration of medicine, vitals, procedures, etc.

Figure 1B:
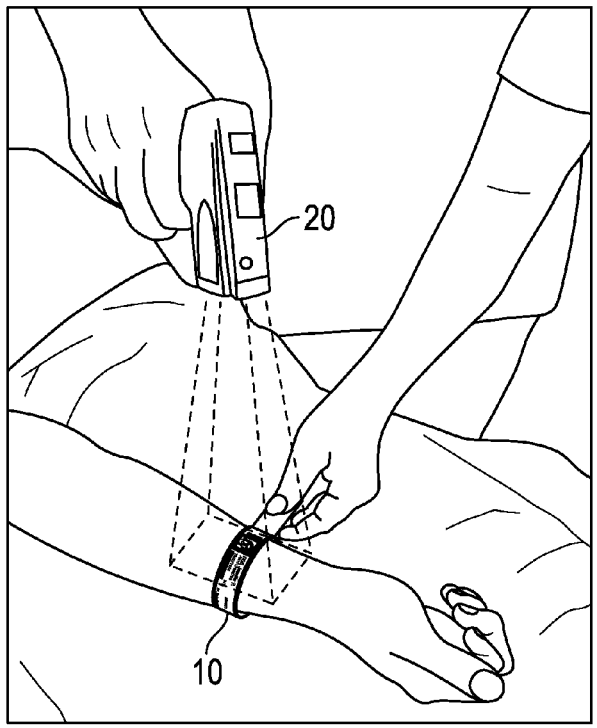
FIG. 1B illustrates a perspective view of a scanner and a scanning process of a barcode on the known arm band.

FIG. 1B illustrates a perspective view of a scanner 20 and a scanning process of the barcode 12 on the arm band 10. To track the patient's identification, the barcode 12 must be physically scanned by a scanner 20 to confirm the patient identification prior to monitoring or recording vitals, administration of medicine or treatments, performing procedures, etc. Thus, a caretaker must have a physical scanner 20 to scan the barcode 12 to identify the patient prior to administering the medicine, recording vitals, performing procedures, etc. This process requires a separate scanner 20 and is time consuming and cumbersome to perform.

Figure 1C:
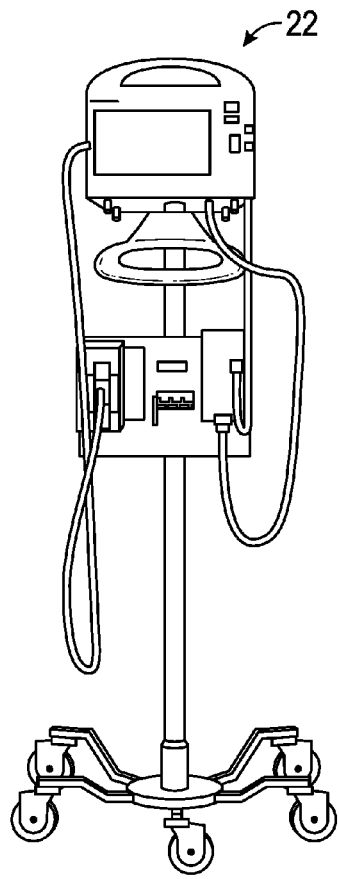
FIG. 1C illustrates a perspective view of an embodiment of a vitals monitoring cart.

FIG. 1C illustrates a perspective view an embodiment of a vitals monitoring cart 22. The vitals cart 22 includes multiple instruments, such as a blood pressure cuff, thermometer, and/or a pulse oximeter. In general, such a vitals cart 22 must be wheeled into a patient's room periodically, e.g. every 1-4 hours. The caretaker must scan the bar code 12 on the armband 10 of the patient using the separate scanner 20. Then the caretaker must use each separate instrument to determine a patient's vitals, such as blood pressure, temperature, pulse rate and blood oxygen level. These measurements must then be manually input into a computer, laptop, etc. to be included in the patient's electronic medical record (EMR). This process is time consuming, disturbs a patient's sleep, is only performed periodically, requires multiple instruments, and manual intervention.

In addition, a caretaker may need to periodically take blood samples of the patient to determine other health measurements, such as glucose levels, liver enzyme levels, etc. Often, multiple blood samples must be taken from a patient throughout a day. This process is painful for the patient, time consuming, inconvenient and is not continuous. As such, there is a need for a patient tracking system that includes a continuous and non-invasive biosensor that may measure a patient's vitals, such as pulse, blood pressure, temperature, as well as concentration of certain substances in the blood, such as insulin resistance or glucose levels, liver enzymes, analytes, or other substances.

Overview

A non-invasive and continuous biosensor is implemented in a compact form factor, such as on a wrist band. Due to its compact form factor, the biosensor may be configured for measurements on various skin surfaces of a patient, including on a forehead, arm, wrist, abdominal area, chest, leg, ear lobe, finger, toe, ear canal, etc. The biosensor includes a memory that stores a patient identification number and patient information, such as name and date of birth, as well as an EMR of the patient. The biosensor includes a near field communication transceiver, such as an RFID transceiver, for wirelessly communicating the patient identification information. The patient identification may thus be easily communicated for admissions, tracking of the patient, recording administration of medication, tracking medical procedures, tracking inventory, tracking care management of the patient, billing, and other functions.

In addition, the biosensor includes one or more sensors for detecting biosensor data, such as a patient's vitals, activity levels, or concentrations of substances in the blood flow of the patient. For example, the biosensor may include a temperature sensor having an array of sensors positioned adjacent to the skin of the patient. The biosensor may also include an activity monitor to determine activity level and/or positioning of the patient. The biosensor may also include a photoplethysmograpy (PPG) sensor. The PPG sensor may be configured to detect oxygen saturation ($SPO_2$) levels in blood flow, as well as heart rate and blood pressure. In addition, the PPG sensor is configured to monitor concentration levels or indicators of one or more substances in the blood flow of the patient, such as insulin resistance, glucose levels, liver enzymes, analytes, white blood cell count, alcohol levels, or other substances. In another aspect, the PPG sensor may detect circulation problems and sleep apnea.

The biosensor data obtained by the biosensor may be associated with the patient identification and wirelessly communicated to one or more other devices for monitoring and updating of the patient's EMR.

Embodiment—Arm Band with Biosensor

Figure 2:
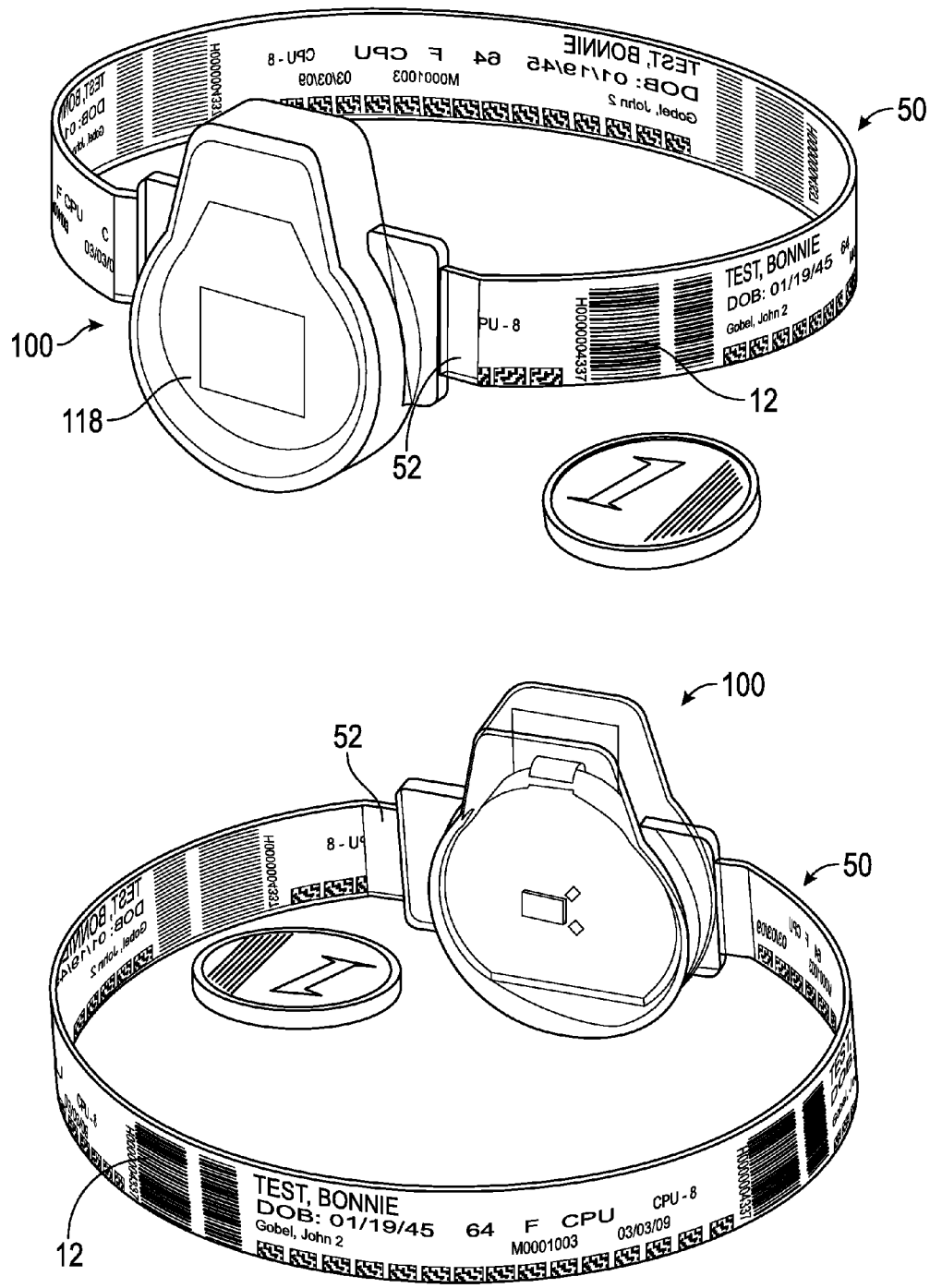
FIG. 2 illustrates a perspective view of an embodiment of a health care band.

FIG. 2 illustrates a perspective view of an embodiment of a health care band 50. The health care band 50 is equipped with a biosensor 100 that includes one or more sensors for collecting vitals of a patient. The biosensor 100 includes a wireless transmitter that is configured to communicate with a healthcare facility network or other LAN, MAN or WAN as well as a near field communication transceiver, such as an RFID transceiver, to communicate with local devices. The biosensor 100 stores a unique identification of the patient that may be programmed at admission to the hospital or upon assignment of the health care band 500 to the patient. The unique identification is associated with the patient's EMR such that biosensor data obtained by the biosensor 100 may be transmitted with the patient's unique identification for monitoring or storage in the patient's EMR.

The biosensor 100 is configured to monitor patient vitals, activity levels and detect indicators or concentration levels of one or more substances in the blood of the patient. The patient's vitals are thus monitored by the biosensor on the armband without manual intervention or additional instruments or drawing blood of the patient. The biosensor may be used to track progress of the patient throughout treatment at a hospital or other healthcare facility and provide medical alerts to notify when vitals are critical.

The health care band 50 may be configured with an adjustable band for placement or attachment to a patient on an arm, on one or more fingers, around a leg, etc. The health care band 50 may be disposable and unique to each patient. In addition, the health care band 50 may also include a barcode 12 for compatibility with existing systems or for duplication/back-up purposes.

In one aspect, the biosensor 100 is removeably attached to the health care band 50 using an attachment mechanism 52. For example, the attachment mechanism 52 may include clips or a holder that the band slides through or other means for attachment and detachment of the biosensor 100 to the health care band 50.

Embodiment—Biosensor Components

Figure 3:
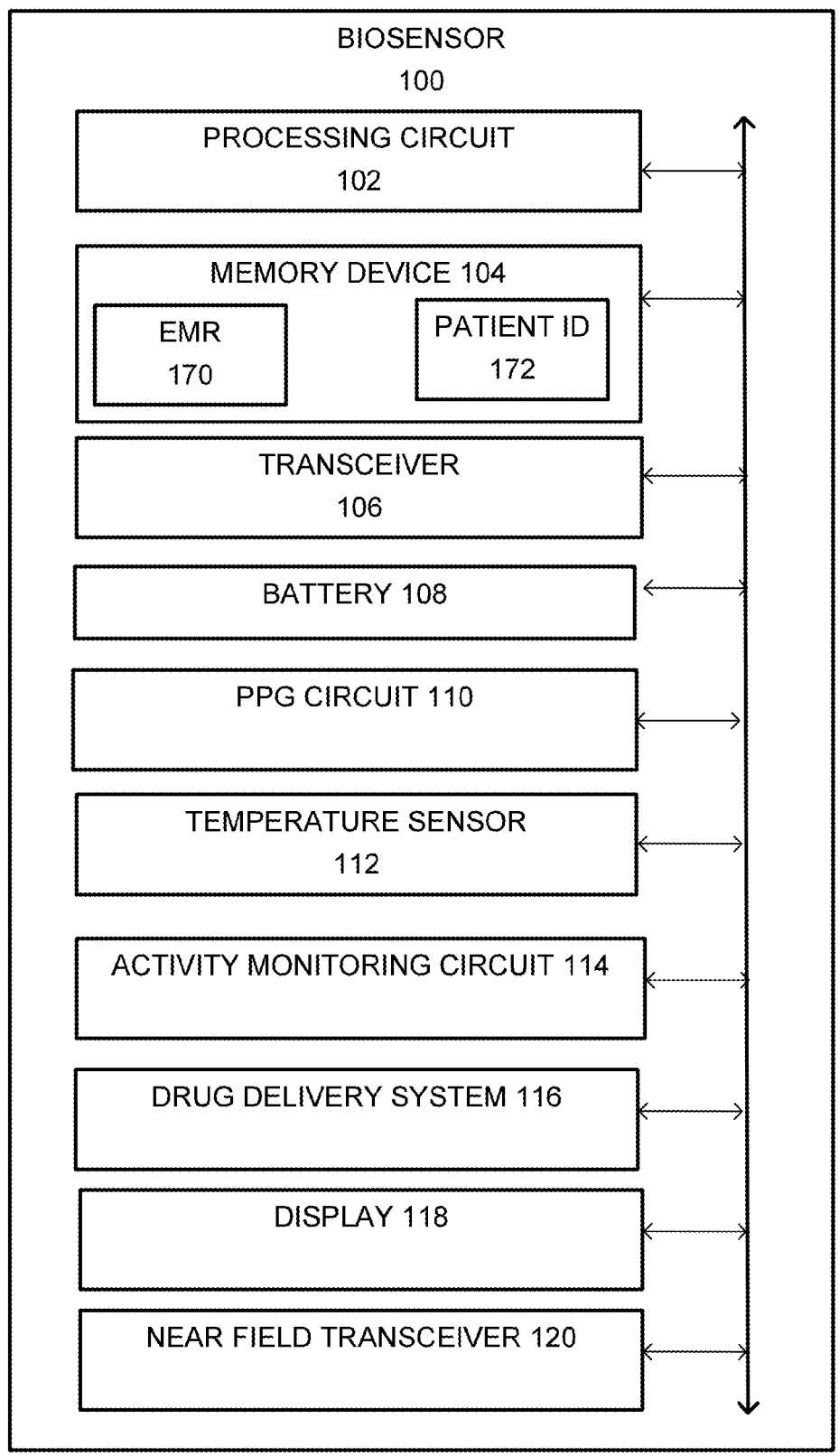
FIG. 3 illustrates a schematic block diagram of an exemplary embodiment of a biosensor.

FIG. 3 illustrates a schematic block diagram of an exemplary embodiment of a biosensor 100. The biosensor 100 includes one or more processing circuits 102 communicatively coupled to a memory device 104. In one aspect, the memory device 104 may include one or more non-transitory processor readable memories that store instructions which when executed by the processing circuit 102, causes the processing circuit 102 to perform one or more functions described herein. The memory device 104 may also include an EEPROM to store a patient identification (ID) 172 that is associated with a patient being monitored by the biosensor 100. The memory device 104 may also store an electronic medical record (EMR) or portion of the EMR associated with the patient being monitored by the biosensor 100. The biosensor data obtained by the biosensor 100 may be stored in the EMR as well as the patient medical history. The processing circuit 102 may be co-located with one or more of the other circuits in the biosensor 100 in a same physical encasement or located separately in a different physical encasement or located remotely. In an embodiment, the biosensor 100 is battery operated and includes a battery 108, such as a lithium ion battery. The biosensor 100 may also include a display configured to display the biosensor data.

The biosensor 100 further includes a transceiver 106. The transceiver 106 may include a wireless or wired transceiver configured to communicate with one or more devices over a LAN, MAN and/or WAN. In one aspect, the wireless transceiver may include IEEE 802.11ah, Zigbee, IEEE 802.15-11 or WLAN (such as an IEEE 802.11 standard protocol) compliant transceiver. In another aspect, the wireless transceiver may also include or alternatively include an interface for communicating over a cellular network. In an embodiment, the wireless transceiver may include a thin foil for an antenna that is specially cut and includes a carbon pad contact to a main PCB of the biosensor 100. This type of antenna is inexpensive to manufacture and may be printed on the inside of an enclosure for the biosensor 100 situated away from the skin of the patient to minimize absorption. The transceiver 106 may also include a wired transceiver interface, e.g., a USB port or other type of wired connection, for communication with one or more other devices over a LAN, MAN and/or WAN.

The biosensor 100 includes one or more types of sensors, such as a PPG circuit 110, a temperature sensor 112 or an activity monitoring circuit 114. The temperature sensor 112 is configured to detect a temperature of a patient. For example, the temperature sensor 112 may include an array of sensors (e.g., 16×16 pixels) positioned on a side of the biosensor 100 such that the array of sensors are adjacent to the skin of the patient. The array of sensors then detects an indication of the temperature of the patient from the skin.

The activity monitoring circuit 114 is configured to monitor the activity level of the patient. For example, the activity monitoring circuit 114 may include a multiple axes accelerometer that measures a position of the patient and motion of the patient. In one aspect, the activity monitoring circuit 114 determines periods of activity and rest. For example, the activity monitoring circuit 114 monitors and records periods of rest that meet a predetermined threshold of low motion or activity level, such as sitting, lying, sleeping, etc. The activity monitoring circuit 114 may also monitor and record periods of activity that meet a predetermined threshold of motion or activity level, such as walking, running, lifting, squatting, etc. The biosensor 100 is then configured to measure and store the patient vitals with an indicator of the activity level of the patient. For example, blood oxygen levels may vary greatly in patients with COPD during rest and activity. The vitals of the patient are tracked during periods of activity and rest and the level of activity at time of measuring the vitals is recorded. The biosensor 100 is thus configured to associate measurements of patient vitals with the activity level of the patient.

In another aspect, to help lower power consumption, in an embodiment, the biosensor 100 includes a rest mode. For example, the activity monitoring circuit 114 may signal a rest mode when a patient is asleep or meets a predetermined threshold of low activity level for a predetermined time period. In the rest mode, the biosensor 100 signals one or more modules to halt non-essential processing functions. When the activity monitoring circuit 114 detects a higher activity level exceeding another predetermined threshold for a predetermined time period, the biosensor 100 signals one or more modules to exit rest mode and resume normal functions. This activity monitoring feature helps to save power and extend battery life of the biosensor 100.

In another aspect, the activity monitoring circuit is configured to include a fitness tracker application. The activity monitoring circuit 114 may monitor a number of steps of the patient, amount and length of periods of sleep, amount and length of periods of rest, amount and length of periods of activity, etc.

The biosensor 100 may also include an integrated drug delivery system 116 or be communicatively coupled to a drug delivery system 116. The biosensor 100 may be configured to control delivery of medicine to a patient based on biosensor data obtained by the biosensor 100 as described in more detail in U.S. Provisional Application No. 62/383,313 entitled, "System and Method for a Drug Delivery and Biosensor Patch," filed Sep. 2, 2016, which is expressly incorporated by reference herein.

The biosensor 100 may include a display 118. The biosensor 100 is configured to display a graphical user interface (GUI) that includes biosensor data.

The biosensor 100 also includes a near field transceiver 120 that may operate using RFID, short range radio frequency, Bluetooth, infrared link, or other short range wireless communication protocol. The near field transceiver 120 may transmit the patient identification and biosensor data over a short range to local devices.

The biosensor 100 also includes a PPG circuit 110. The PPG circuit 110 may be configured to detect oxygen saturation ($SaO_2$ or $SpO_2$) levels in blood flow, as well as heart rate and blood pressure. In addition, the PPG circuit 110 is configured to detect concentration levels or indicators of one or more substances in the blood flow of the patient as described in more detail herein.

Embodiment—PPG Circuit

Figure 4:
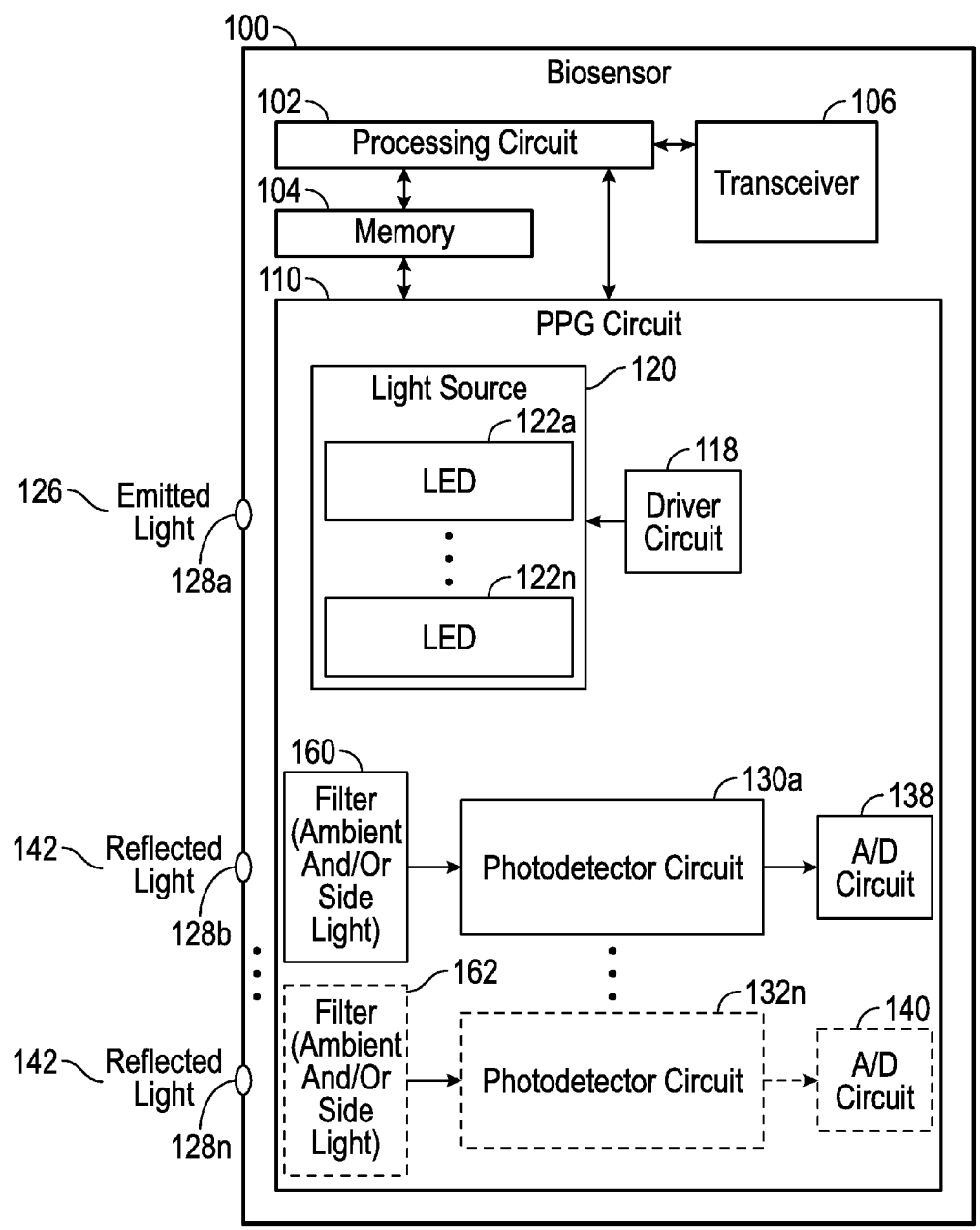
FIG. 4 illustrates a schematic block diagram illustrating an embodiment of the PPG circuit in more detail.

FIG. 4 illustrates a schematic block diagram illustrating an embodiment of the PPG circuit 110 in more detail. The PPG circuit 110 implements photoplethysmography (PPG) techniques for obtaining concentration levels or indicators of one or more substances in pulsating arterial blood flow. The PPG circuit 110 includes a light source 120 having a plurality of light sources, such as LEDs 122a-n, configured to emit light through at least one aperture 128a. The PPG circuit 110 is configured to direct the emitted light at an outer or epidermal layer of skin tissue of a patient. The plurality of light sources are configured to emit light in one or more spectrums, including infrared (IR) light, ultraviolet (UV) light, near IR light or visible light, in response to driver circuit 118. For example, the biosensor 100 may include a first LED 122a that emits visible light and a second LED 122b that emits infrared light and a third LED 122c that emits UV light, etc. In another embodiment, one or more of the light sources 122a-n may include tunable LEDs or lasers operable to emit light over one or more frequencies or ranges of frequencies or spectrums in response to driver circuit 118.

In an embodiment, the driver circuit 118 is configured to control the one or more LEDs 122a-n to generate light at one or more frequencies for predetermined periods of time. The driver circuit 118 may control the LEDs 122a-n to operate concurrently or progressively. The driver circuit 118 is configured to control a power level, emission period and frequency of emission of the LEDs 122a-n. The biosensor 100 is thus configured to emit one or more frequencies of light in one or more spectrums that is directed at the surface or epidermal layer of the skin tissue of a patient.

The PPG circuit 110 further includes one or more photodetector circuits 130a-n. For example, a first photodetector circuit 130 may be configured to detect visible light and the second photodetector circuit 130 may be configured to detect IR light. The first photodetector circuit 130 and the second photodetector circuit 130 may also include a first filter 160 and a second filter 162 configured to filter ambient light and/or scattered light. For example, in some embodiments, only light received at an approximately perpendicular angle to the skin surface of the patient is desired to pass through the filters. The first photodetector circuit 130 and the second photodetector circuit 132 are coupled to a first A/D circuit 138 and a second A/D circuit 140. The A/D circuits 138 and 140 may also include an amplifier and other components needed to generate the spectral response. In another aspect, the plurality of photodetectors 130 is coupled in parallel to a single amplifier and A/D circuit 138. The light detected by each of the photodetectors 130 is thus added and amplified to generate a single spectral response.

In another embodiment, a single photodetector circuit 130 may be implemented operable to detect light over multiple spectrums or frequency ranges. For example, the photodetector circuit 130 may include a Digital UV Index/IR/Visible Light Sensor such as Part No. Si1145 from Silicon Labs™.

The one or more photodetector circuits 130 include a spectrometer or other type of circuit configured to detect an intensity of light as a function of wavelength or frequency to obtain a spectral response. The one or more photodetector circuits 130 detects the intensity of light either transmitted through or reflected from tissue of a patient that enters one or more apertures 128b-n of the biosensor 100. For example, the light may be detected from transmissive absorption (e.g., through a fingertip or ear lobe) or from reflection (e.g., reflected from a forehead or stomach tissue). The photodetector circuits 130 then obtain a spectral response of the detected light by measuring the intensity of light either transmitted or reflected to the photodiodes.

Figure 5:
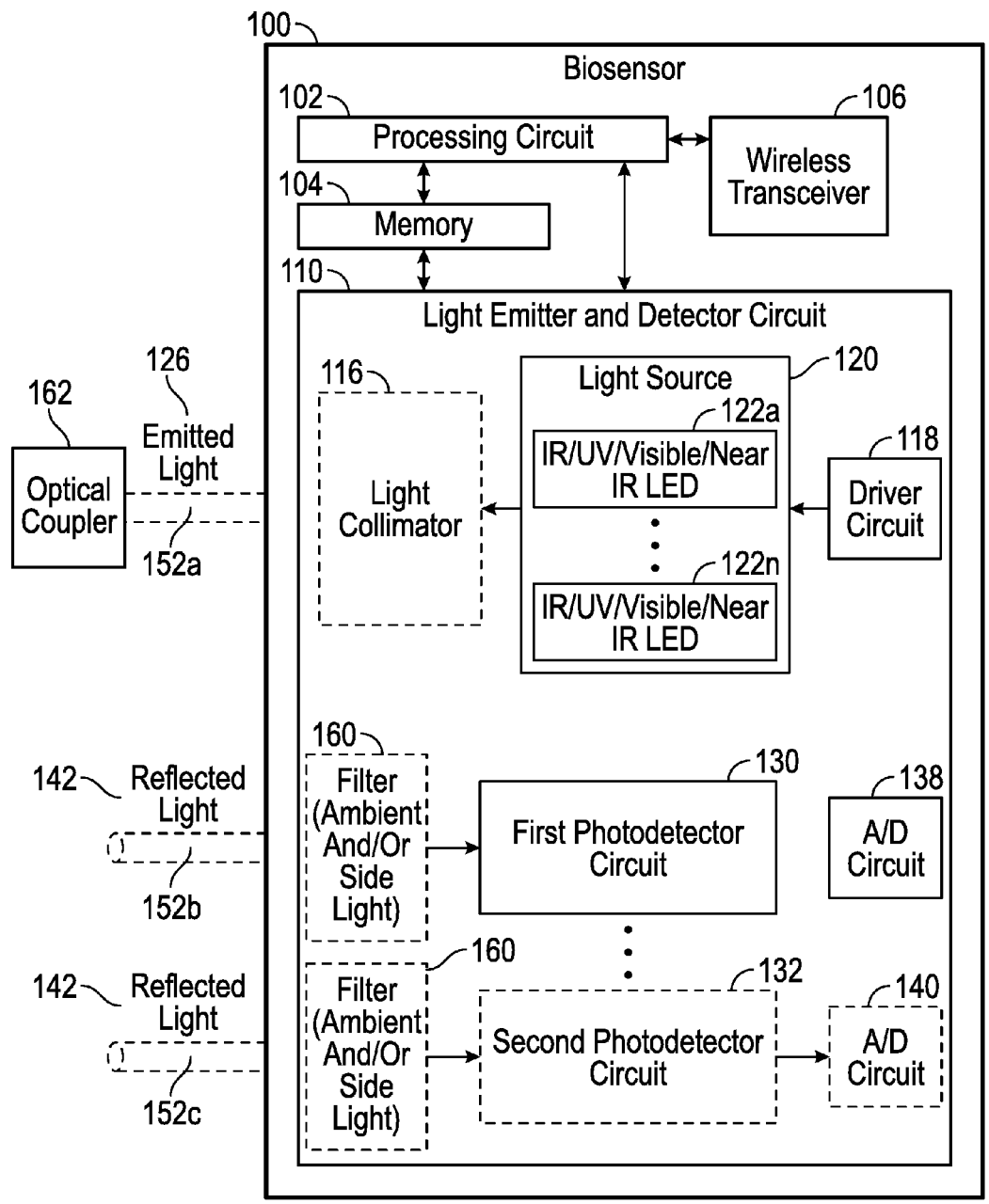
FIG. 5 illustrates a schematic block diagram of another exemplary embodiment of the the PPG circuit.

FIG. 5 illustrates a schematic block diagram of another exemplary embodiment of the the PPG circuit 110. In this embodiment, the biosensor 100 is configured for emitting and detecting light through one or more optical fibers 152a-c. The PPG circuit 110 is optically coupled to a plurality of optical fibers 152a-c. In an embodiment, the plurality of optical fibers 152 includes a first optical fiber 152a optically coupled to the light source 120. An optical coupler (not shown) to spread the angle of light emitted from the optical fiber 152a may also be implemented. The optical fiber 152a may have a narrow viewing angle such that an insufficient area of skin surface is exposed to the light. An optical coupler 162 may be used to widen the viewing angle to increase the area of skin surface exposed to the light.

A second optical fiber 152b is optically coupled to a first photodetector circuit 130 and a third optical fiber 152c is optically coupled to the second photodetector circuit 132. Other configurations and numbers of the plurality of optical fibers 152 may also be implemented.

In one aspect, the plurality of optical fibers 152 is situated within an outer ear canal to transmit and detect light in the ear canal. A light collimator 116, such as a prism, may be used to align a direction of the light emitted from the light source 120. One or more filters 160 may optionally be implemented to receive the reflected light 142 from the plurality of optical fibers 152b, 152c. However, the filters 160 may not be needed as the plurality of optical fibers 152b, 152c may be sufficient to filter ambient light and/or scattered light.

Figure 6:
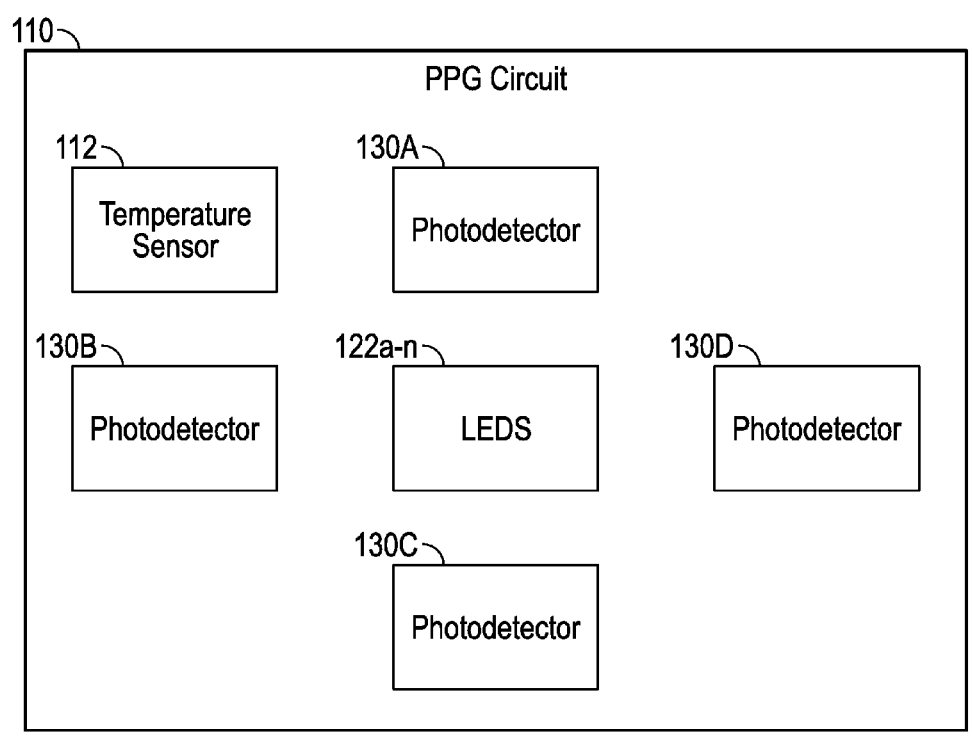
FIG. 6 illustrates a schematic block diagram of an embodiment of the PPG circuit with a plurality of photodetectors.

FIG. 6 illustrates a schematic block diagram of an embodiment of the PPG circuit 110 with a plurality of photodetectors 130. In one aspect, the plurality of photodetectors 130 are situated in different physical positions and orientations in the biosensor 100. For example, at least four photodetectors 130a, 130b, 130c and 130d are situated in the biosensor 100 in four different physical positions in a North-South and East-West orientation or polarity. The output signals of the plurality of photodetectors are coupled in parallel to the amplifier and A/D circuit 138. The light signals detected by each of the photodetectors 130 through an aperture 128 in the biosensor are added and amplified to generate a single spectral response. The spectral response is thus more robust and less affected by motion artifacts and movement of the biosensor 100 on the health care band 50. The LEDs 122a-n may be situated centrally to the physical position of the plurality of photodetectors. The temperature sensor 112 may also be physically situated near the PPG circuit 110 to detect temperature through a same aperture 128.

Embodiment—PPG Measurement of Arterial Blood Flow

One or more of the embodiments of the biosensor 100 described herein are configured to detect a concentration level or indicator of one or more substances within blood flow, such as analyte levels, nitric oxide levels, insulin resistance or insulin response after caloric intake and predict diabetic risk or diabetic precursors. The biosensor 100 may detect insulin response, vascular health, cardiovascular sensor, cytochrome P450 proteins (e.g. one or more liver enzymes or reactions), digestion phase 1 and 2 or caloric intake. The biosensor 100 may even be configured to detect proteins or other elements or compounds associated with cancer. The biosensor 100 may also detect various electrolytes and many common blood analytic levels, such as bilirubin amount and sodium and potassium. For example, the biosensor 100 may detect sodium NACL concentration levels in the arterial blood flow to determine dehydration. The biosensor 100 may also detect blood alcohol levels in vivo in the arterial blood flow. Because blood flow to the skin can be modulated by multiple other physiological systems, the PPG sensor 110 may also be used to monitor breathing, hypovolemia, and other circulatory conditions. The biosensor 100 may also detect blood pressure, peripheral oxygen ($SpO_2$ or $SaO_2$) saturation, heart rate, respiration rate or other patient vitals. The PPG circuit 110 may also be used to detect sleep apnea based on oxygen saturation levels and activity monitoring during sleep.

In use, the biosensor 100 performs PPG techniques using the PPG circuit 110 to detect the concentration levels of substances in blood flow. In one aspect, the biosensor 100 analyzes reflected visible or IR light to obtain a spectrum response such as, the resonance absorption peaks of the reflected visible, UV or IR light. The spectrum response includes spectral lines that illustrate an intensity or power or energy at a wavelength or range of wavelengths in a spectral region of the detected light.

The ratio of the resonance absorption peaks from two different frequencies can be calculated and based on the Beer-Lambert law used to obtain various levels of substances in the blood flow. First, the spectral response of a substance or substances in the arterial blood flow is determined in a controlled environment, so that an absorption coefficient $\alpha_{g1}$ can be obtained at a first light wavelength $\lambda_1$ and at a second wavelength $\lambda_2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined using the following equations:

At the first wavelength $\lambda_1, I_1 = I_{in1} * 10^{-(\alpha_{g1}C_{gw} + \alpha_{w1}C_w)*l}$ At the second wavelength $\lambda_2, I_2 = I_{in2} * 10^{-(\alpha_{g2}C_{gw} + \alpha_{w2}C_w)*l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I1}{Iin1}\right)}{\log 10\left(\frac{I2}{Iin2}\right)}$$

The concentration of the substance Cg may then be equal to:

$$Cg = \frac{Cgw}{Cgw + Cw} = \frac{\alpha_{w2}R - \alpha_{w1}}{(\alpha_{w2} - \alpha_{gw2}) * R - (\alpha_{w1} - \alpha_{gw1})}$$

The biosensor 100 may thus determine the concentration of various substances in arterial blood using spectroscopy at two different wavelengths using Beer-Lambert principles.

The biosensor 100 determines concentration of one or more substances using Beer-Lambert principles. The biosensor 100 transmits light at least at a first predetermined wavelength and at a second predetermined wavelength. The biosensor 100 detects the light (reflected from the skin or transmitted through the skin) and analyzes the spectral response at the first and second wavelengths to detect an indicator or concentration level of one or more substances in the arterial blood flow. In general, the first predetermined wavelength is selected that has a high absorption coefficient for the targeted substance while the second predetermined wavelength is selected that has a low absorption coefficient for the targeted substance. Thus, it is generally desired that the spectral response for the first predetermined wavelength have a higher intensity level than the spectral response for the second predetermined wavelength.

In another aspect, the biosensor 100 may transmit light at the first predetermined wavelength and in a range of approximately 1 nm to 50 nm around the first predetermined wavelength. Similarly, the biosensor 100 may transmit light at the second predetermined wavelength and in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted light by the target substance may by spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated. The biosensor 100 analyzes the first and second spectral responses to detect an indicator or concentration level of one or more substances in the arterial blood flow at 406.

Photoplethysmography (PPG) is used to measure time-dependent volumetric properties of blood in blood vessels due to the cardiac cycle. For example, the heartbeat affects volume of arterial blood flow and the concentration of absorption levels being measured in the arterial blood flow. Over a cardiac cycle, pulsating arterial blood changes the volume of blood flow in an artery. Incident light $I_O$ is directed at a tissue site and a certain amount of light is reflected or transmitted and a certain amount of light is absorbed. At a peak of arterial blood flow or arterial volume, the reflected/transmitted light $I_L$ is at a minimum due to absorption by the venous blood, nonpulsating arterial blood, pulsating arterial blood, other tissue, etc. At a minimum of arterial blood flow or arterial volume during the cardiac cycle, the transmitted/reflected light $I_H$ is at a maximum due to lack of absorption from the pulsating arterial blood.

The biosensor 100 is configured to filter the reflected/transmitted light $I_L$ of the pulsating arterial blood from the transmitted/reflected light $I_H$. This filtering isolates the light due to reflection/transmission of substances in the pulsating arterial blood from the light due to reflection/transmission from venous (or capillary) blood, other tissues, etc. The biosensor 100 may then measure the concentration levels of one or more substances from the reflected/transmitted light $I_L$ in the pulsating arterial blood. Though the above has been described with respect to arterial blood flow, the same principles described herein may be applied to venous blood flow.

In general, the relative magnitudes of the AC and DC contributions to the reflected/transmitted light signal I may be used to substantially determine the differences between the diastolic time and the systolic points. In this case, the difference between the reflected light $I_L$ and reflected light $I_H$ corresponds to the AC contribution of the reflected light (e.g. due to the pulsating arterial blood flow). A difference function may thus be computed to determine the relative magnitudes of the AC and DC components of the reflected light I to determine the magnitude of the reflected light $I_L$ due to the pulsating arterial blood. The described techniques herein for determining the relative magnitudes of the AC and DC contributions is not intended as limiting. It will be appreciated that other methods may be employed to isolate or otherwise determine the relative magnitude of the light $I_L$ due to pulsating arterial blood flow.

Figure 7:
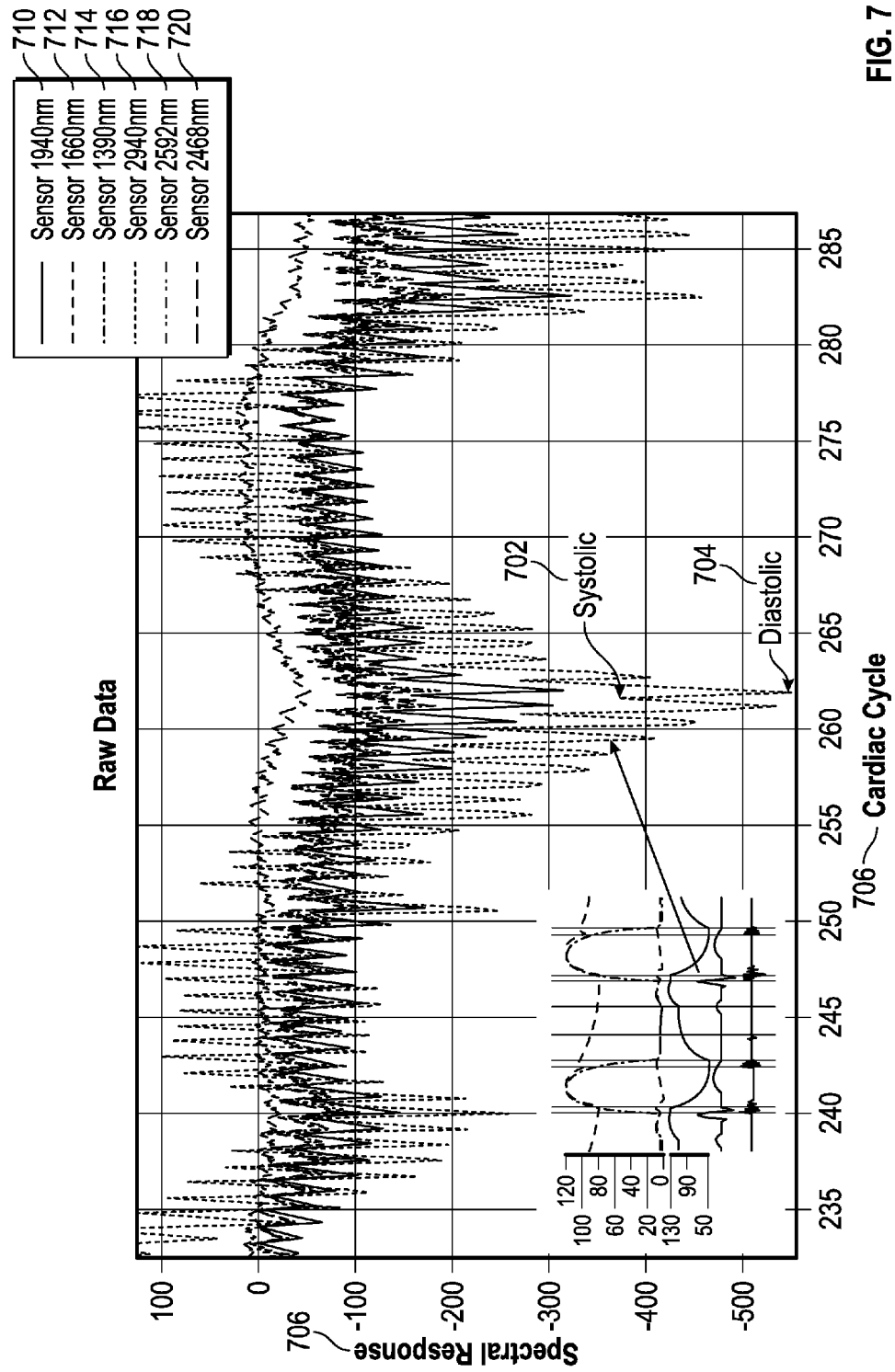
FIG. 7 illustrates a schematic diagram of a graph of actual clinical data obtained using PPG techniques at a plurality of wavelengths.

FIG. 7 illustrates a schematic diagram of a graph of actual clinical data obtained using PPG techniques at a plurality of wavelengths. The biosensor 100 emits light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral response 706 for the plurality of wavelengths obtained using the biosensor in clinical trials is shown in FIG. 7. In this clinical trial, two biosensors 100 attached to two separate fingertips of a patient were used to obtain the spectral responses 706. The first biosensor 100 obtained the spectral response for a wavelength at 940 nm 710, a wavelength at 660 nm 712 and a wavelength at 390 nm 714. The second biosensor 100 obtained the spectral response for a wavelength at 940 nm 716, a wavelength at 592 nm 718 and a wavelength at 468 nm 720.

In one aspect, the spectral response of each wavelength may be aligned based on the systolic 702 and diastolic 704 points in their spectral responses. This alignment is useful to associate each spectral response with a particular stage or phase of the pulse-induced local pressure wave within the blood vessel (which may mimic the cardiac cycle 706 and thus include systolic and diastolic stages and sub-stages thereof). This temporal alignment helps to determine the absorption measurements acquired near a systolic point in time of the cardiac cycle and near the diastolic point in time of the cardiac cycle 706 associated with the local pressure wave within the patient's blood vessels. This measured local pulse timing information may be useful for properly interpreting the absorption measurements in order to determine the relative contributions of the AC and DC components measured by the biosensor 110. So for one or more wavelengths, the systolic points 702 and diastolic points 704 in the spectral response are determined. These systolic points 702 and diastolic points 704 for the one or more wavelengths may then be aligned as a method to discern concurrent responses across the one or more wavelengths.

In another embodiment, the systolic points 702 and diastolic points 704 in the absorbance measurements are temporally correlated to the pulse-driven pressure wave within the arterial blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary.

Figure 8:
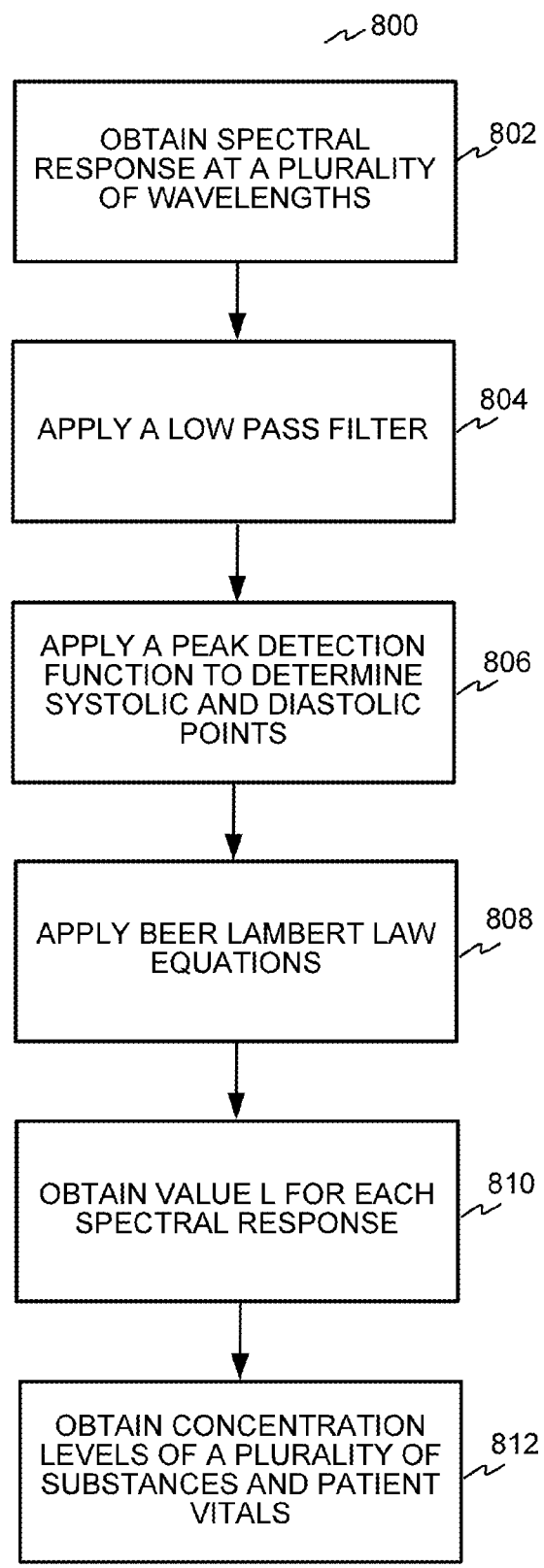
FIG. 8 illustrates a logical flow diagram of an embodiment of a method of the biosensor.

FIG. 8 illustrates a logical flow diagram of an embodiment of a method 800 of the biosensor 100. In one aspect, the biosensor 100 emits and detects light at a plurality of predetermined frequencies or wavelengths, such as approximately 940 nm, 660 nm, 390 nm, 592 nm, and 468 nm. The light is pulsed for a predetermined period of time (such as 100 usec or 200 Hz) sequentially at each predetermined wavelength. In another aspect, light may be pulsed in a wavelength range of 1 nm to 50 nm around each of the predetermined wavelengths. Then, the spectral responses are obtained for the plurality of wavelengths at 802. The spectral response may be measured over a predetermined period (such as 300 usec.). This measurement process is repeated sequentially pulsing the light and obtaining spectral measurements over a desired measurement period, e.g. from 1-2 seconds to 1-2 minutes or 2-3 hours or continuously over days or weeks. Because the human pulse is typically on the order of magnitude of one 1 HZ, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period.

A low pass filter (such as a 5 Hz low pass filter) is applied to the spectral response signal at 804. The relative contributions of the AC and DC components are obtained $I_{AC+DC}$ and $I_{AC}$. A peak detection algorithm is applied to determine the systolic and diastolic points at 706. Beer Lambert equations are applied as described below at 708. For example, the $L_\lambda$ values are then calculated for one or more of the wavelengths λ, wherein the $L_\lambda$ values for a wavelength equals:

$$L_\lambda = \mathrm{Log}10\left(\frac{IAC + DC}{IDC}\right)$$

wherein $I_{AC+DC}$ is the intensity of the detected light with AC and DC components and $I_{DC}$ is the intensity of the detected light with the AC filtered by the low pass filter. The value $L_\lambda$ isolates the spectral response due to pulsating arterial blood flow, e.g. the AC component of the spectral response.

A ratio R of the $L_\lambda$ values at two wavelengths may then be determined. For example, $$\mathrm{Ratio}\ R = \frac{L\lambda 1}{L\lambda 2}$$

The $L_\lambda$ values and Ratio R may be determined for one or more of the predetermined measurement periods over a desired time period, e.g. from 1-2 seconds to 1-2 minutes or 2-3 hours or continuously over days or weeks to monitor the values. The $L_\lambda$ values and Ratio R may be used to determine concentration levels of one or more substances in the arterial blood flow as well as patient vitals, such as oxygen saturation SpO2, heart rate, respiration rate, etc.

Embodiment—Determination of Indicators or Concentration Levels of One or More Substances In one aspect, based on unexpected results from clinical trials, it was determined that a ratio $R_{390,940}$ obtained at approximately $L_{\lambda 1}$=390 nm and $L_{\lambda 2}$=940 is useful as a predictor or indicator of diabetic risk or diabetes. For example, during experimental clinical trials, spectral responses were obtained during predetermined measurement periods over a 1-2 minute time period at 390 nm and 940 nm. An $R_{390,940}$ value was obtained based on the spectral responses measured during a plurality of the predetermined measurement periods over the 1-2 minute time period. From the unexpected results of the clinical trials, an average or mean $R_{390,940}$ value of less than 1 (e.g., approximately 0.5) indicated that a person has diabetes or early onset of diabetes. An average or mean $R_{390,940}$ value of 2 or above indicated that a person has a lower risk of a diabetes diagnosis. An average or mean $R_{390,940}$ value in the 5-6 range indicated no current risk of diabetes. The $R_{390,940}$ value determined using $L_{\lambda 1}$=390 nm and $L_{\lambda 2}$=940 was thus an indicator of diabetic risk and diabetes. Thus, based on the clinical trials, a non-invasive, quick 1-2 minute test produced an indicator of diabetes or diabetic risk in a person.

In particular, in unexpected results, it is believed that nitric oxide NO levels in the arterial blood flow is being measured at least in part by the biosensor 100 at $\lambda 1$=390 nm. Since NO is partly in a gaseous form in blood vessels (prior to adhesion to hemoglobin), the total NO concentration levels of in vitro blood samples, e.g. from a finger prick, are not detected as the gas dissipates. Thus, the biosensor 100 measurements to determine the $L_{390\ nm}$ values are the first time NO concentration levels in arterial blood flow have been measured directly in vivo. In clinical trials performed as described further herein, in unexpected results, it seems that the NO levels are an indication of insulin response in the blood as well as concentration levels of insulin and/or glucose levels in the blood. The $L_{\lambda 1=390\ nm}$ and R value obtained from $L_{\lambda 1=390\ nm}$ are thus an indicator of blood glucose levels, insulin response and diabetic risk as well as vascular health. These unexpected results have advantages in early detection of diabetic risk and easier, non-invasive monitoring of insulin resistance and glucose levels as well as vascular health and other conditions. These results are discussed in more detail herein with illustrative experimental data.

The biosensor 100 may also function as a pulse oximeter using similar principles under Beer-lambert law to determine pulse and oxygen saturation levels in pulsating arterial flow. For example, a first wavelength at approximately 940 nm and a second wavelength at approximately 660 nm may be used to determine oxygen saturation levels.

The biosensor 100 may also be used to determine alcohol levels in the blood using wavelengths at approximately 390 nm and/or 468 nm. In another embodiment, an $R_{468,940}$ value for at least $L_{468\ nm}/L_{940\ nm}$ may be used as a liver enzyme indicator, e.g. P450 enzyme indicator. In another embodiment, an $R_{592,940}$ value for at least $L_{592\ nm}/L_{940\ nm}$ may be used as a digestive indicator to measure digestive responses, such as phase 1 and phase 2 digestive stages. The biosensor 100 may also detect other types of electrolytes or analytes, such as sodium and potassium, using similar PPG techniques. In another aspect, the biosensor 100 may detect which blood cell levels in arterial blood flow using similar PPG techniques.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100.

Since the biosensor 100 may operate in multiple frequencies, various health monitoring tests may be performed concurrently and continuously. These tests may be performed throughout a hospital stay or may be non-invasively and quickly and easily obtained using the biosensor 100 in a physician's office or other clinical setting or at home. These and other aspects of the biosensor 100 are described in more detail herein with clinical trial results.

Figure 9:
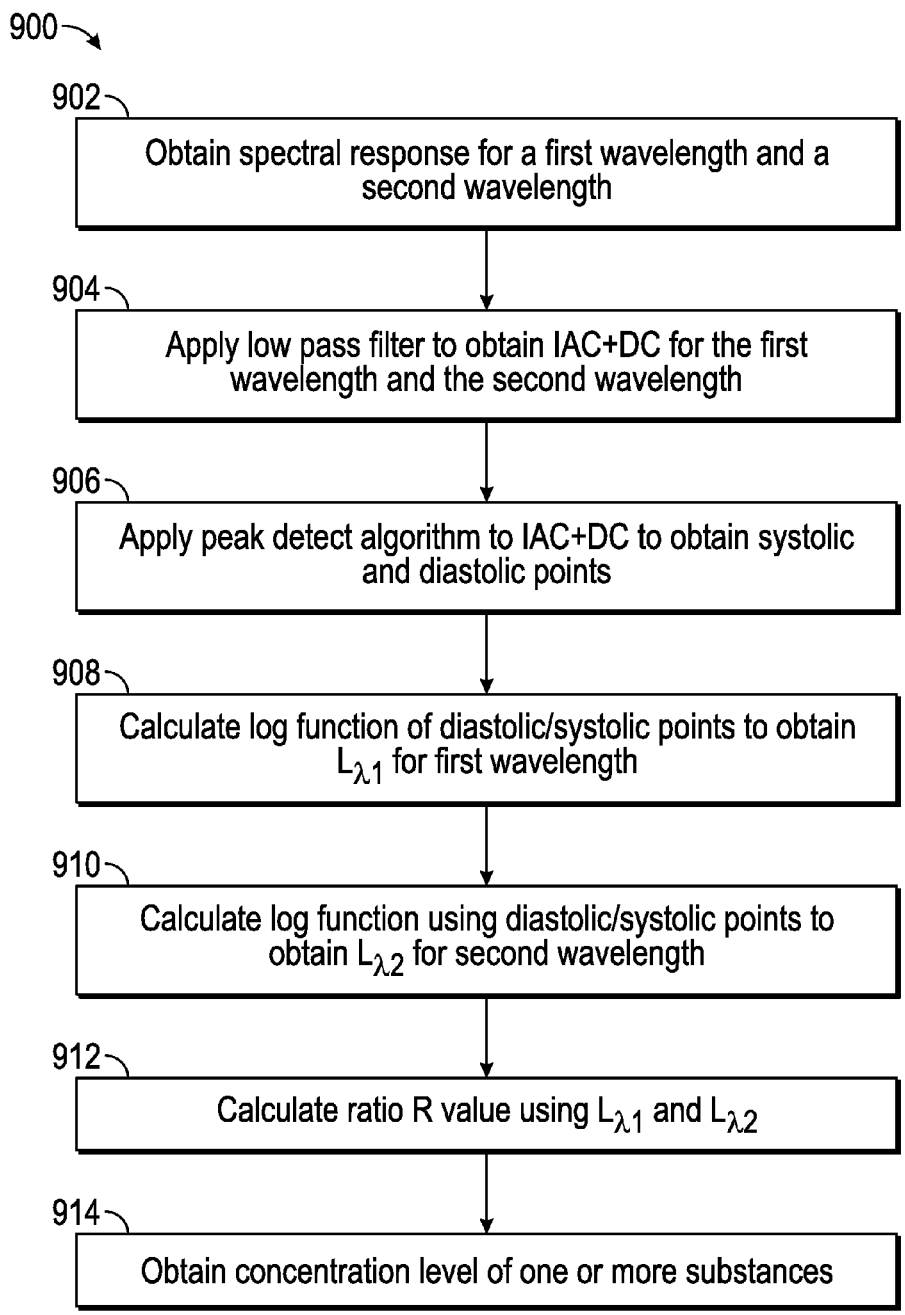
FIG. 9 illustrates a logical flow diagram of an embodiment of a method of determining concentration levels of one or more substances in more detail.

FIG. 9 illustrates a logical flow diagram of an embodiment of a method 900 of determining concentration levels of one or more substances in more detail. The biosensor 100 obtains a first spectral response signal including a first wavelength and a second response signal including a second wavelength at 902. In general, the first wavelength is selected that has a high absorption coefficient for the targeted substance while the second wavelength is selected that has a low absorption coefficient for the targeted substance. Thus, it is generally desired that the spectral response for the first predetermined wavelength have a higher intensity level than the spectral response for the second predetermined wavelength.

Each of the spectral response signals includes AC and DC components $I_{AC+DC}$. A low pass filter is applied to the spectral response signals $I_{AC+DC}$ to isolate the DC component of the first and second spectral response signals $I_{DC}$. The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 906. The systolic and diastolic measurements are compared in order to compute the aforementioned R ratio. For example, a logarithmic function may be applied to the ratio of $I_{AC+DC}$ and $I_{DC}$ to obtain an L value for the first wavelength $L_{\lambda 1}$ at 908 and for the second wavelength $L_{\lambda 2}$ at 910. The ratio R of the $L_{\lambda}$ values may then be calculated at 912.

Figure 10:
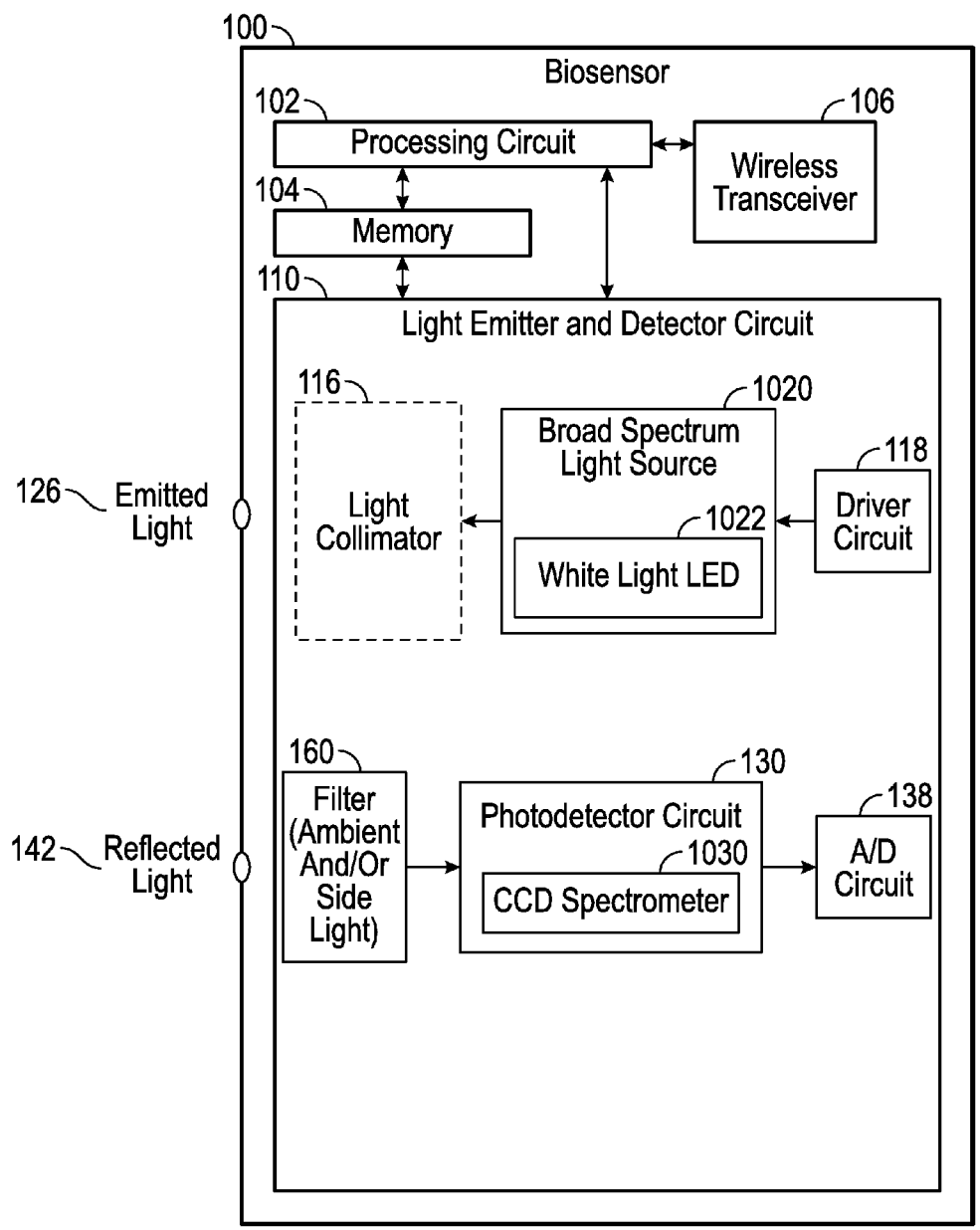
FIG. 10 illustrates a schematic block diagram of another embodiment of a biosensor using a broad spectrum light source.

FIG. 10 illustrates a schematic block diagram of another embodiment of a biosensor 100 using a broad spectrum light source 1020. In one aspect, the biosensor 100 may include a broad spectrum light source 1020, such as a white light to infrared (IR) or near IR LED 1022, that emits light with wavelengths from e.g. 350 nm to 2500 nm. Broad spectrum light sources with different ranges may be implemented. In an aspect, a broad spectrum light source with a range across 100 nm wavelengths to 2000 nm range of wavelengths in the visible, IR and/or UV frequencies. For example, a broadband tungsten light source for spectroscopy may be used. The spectral response of the reflected light is then measured across the wavelengths in the broad spectrum, e.g. from 350 nm to 2500 nm, concurrently. In an aspect, a charge coupled device (CCD) spectrometer 1030 may be configured to measure the spectral response of the detected light over the broad spectrum.

The spectral response of the reflected light is analyzed for a plurality of wavelengths, e.g. at 10 nm to 15 nm to 20 nm, incremental wavelengths across the wavelengths from 10 nm to 2500 nm. For example, the processing described with respect to FIG. 9 is performed at the plurality of wavelengths. In one aspect, the L values are calculated at incremental wavelengths, such as at 1 nm or 1.5 nm or 2 nm incremental wavelengths. This process may be used to determine one or more wavelengths or ranges of wavelengths useful in detection for one or more substances in the arterial blood flow. For example, a spectral response around a wavelength of 500 nm may have a higher intensity. Trials may then be conducted to determine the one or more substances in the blood that generates this spectral response. In another embodiment, a known substance may be present in the blood and the spectral response across the broad spectrum is then analyzed to determine a pattern or correlation of intensities of wavelengths in the spectral response to the known substance. For example, a pattern of intensities of wavelengths across a range of wavelengths may indicate the presence of a substance. The intensities of the wavelengths may then be analyzed to determine concentration levels of the substance as described in more detail herein.

In another embodiment, the spectral response is analyzed at a set of predetermined wavelengths (or a range of 1 nm to 50 nm including each predetermined wavelength). The L values are calculated for the set of predetermined wavelengths using the analyzed spectral responses. The concentration levels of one or more substances may then be determined based on absorption coefficients for the one or more substances at each of the predetermined wavelengths. The concentration levels of a plurality of substances may be determined using the spectral response of a plurality of frequencies. The biosensor 100 may thus be used to detect a plurality of substances based on data obtained during a single measurement period. The biosensor 100 may thus perform a blood panel analysis based on in vivo arterial blood flow in a relatively short measurement period of 1-5 minutes. The blood panel analysis may be performed in a physician's office to determine results of the test while the patient is in the office. The biosensor 100 may thus provide blood panel analysis results in a 1-5 minute measurement period without a need for blood samples and lab tests that may take hours or days or weeks to obtain.

Figure 11A:
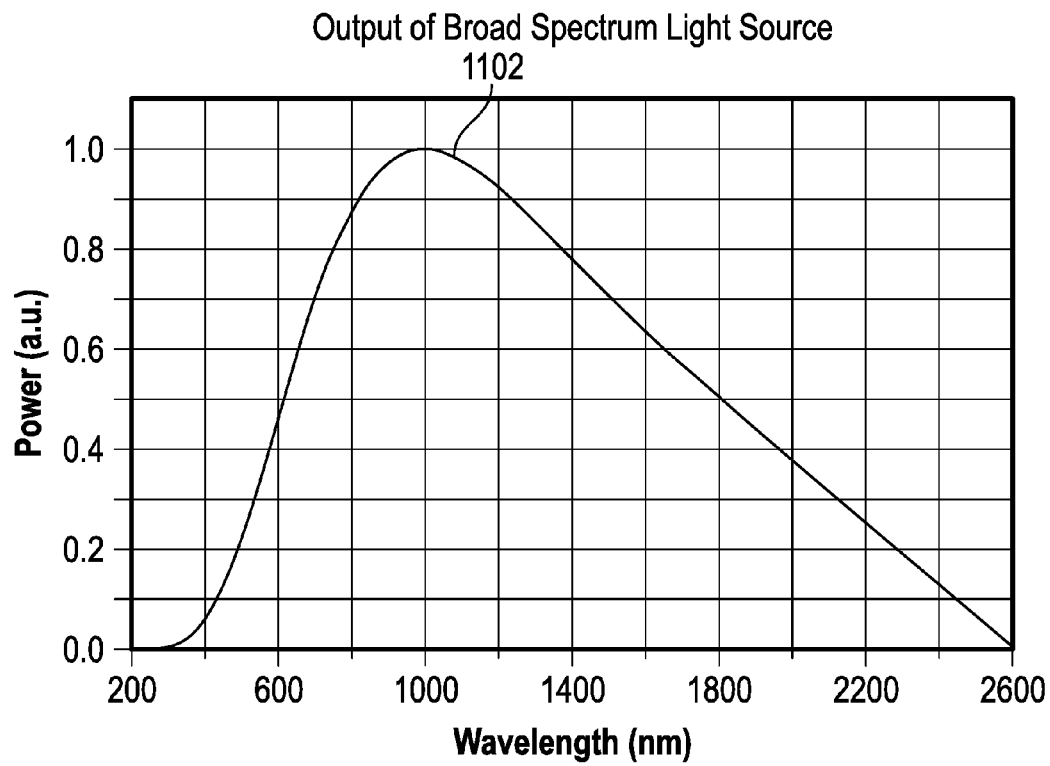
FIG. 11A illustrates a graph of an embodiment of an output of a broad spectrum light source.

FIG. 11A illustrates a graph of an embodiment of an output of a broad spectrum light source. The relative light intensity or power output of the broad spectrum light source is shown versus wavelength of the output light Io. The light intensity or power of the output light extends from wavelengths of approximately 350 nm to approximately 2500 nm. The broad spectrum light source 1020 emits light with power across the wavelengths from 350 nm to 2500 nm. Broad spectrum light sources with different ranges may be implemented. In an aspect, a broad spectrum light source with a range across 100 nm wavelengths to 2000 nm range of wavelengths in the visible, IR and/or UV frequencies.

Figure 11B:
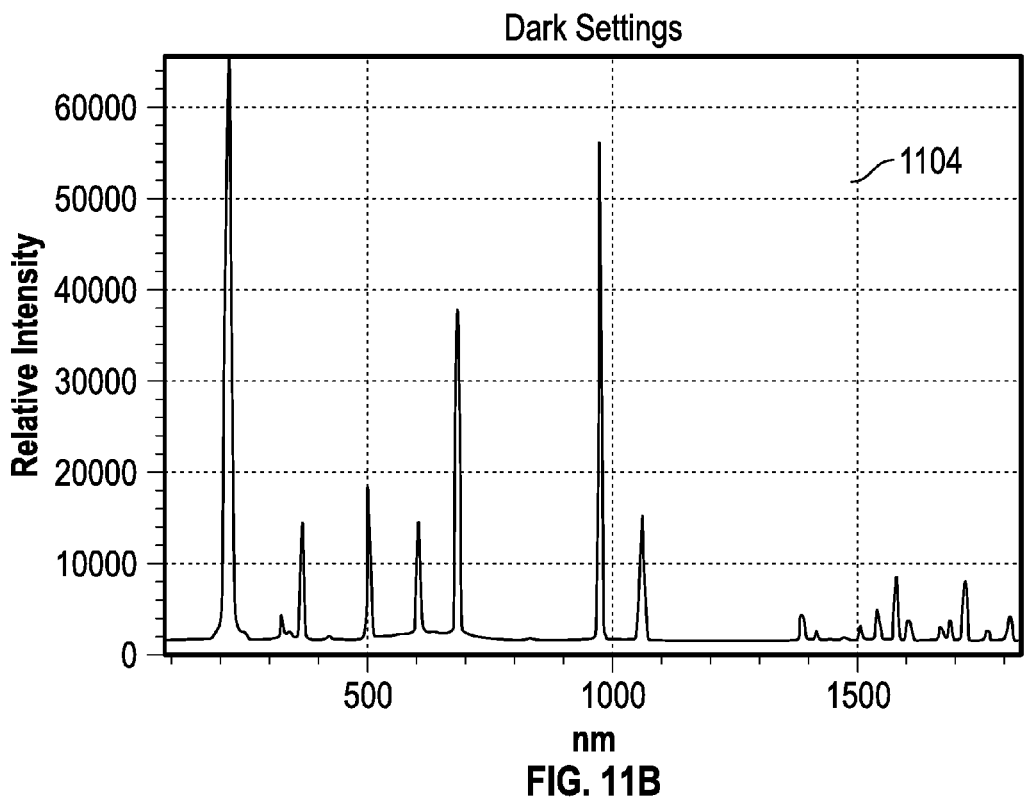
FIG. 11B illustrates a graph with an embodiment of an exemplary spectral response of detected light across a broad spectrum.

FIG. 11B illustrates a graph with an embodiment of an exemplary spectral response of detected light 1104 across a broad spectrum, e.g. from approximately 10 nm to 2000 nm. In one aspect, the spectral response of the detected light 1104 may be analyzed at a plurality of wavelengths, e.g. at a set of predetermined wavelengths or at incremental wavelengths. In another aspect, the spectral response of wavelengths with a detected intensity or power exceeding a predetermined threshold may be analyzed. For example, in the graph shown in FIG. 11B, the spectral response at wavelengths of 200 nm, 680 nm and 990 nm (and ranges of +/−20 to 50 nm around these wavelengths) exceeding a relative intensity threshold of 20000 may be analyzed.

Embodiment—Determination of Concentration Levels at a Plurality of Wavelengths

Figure 12:
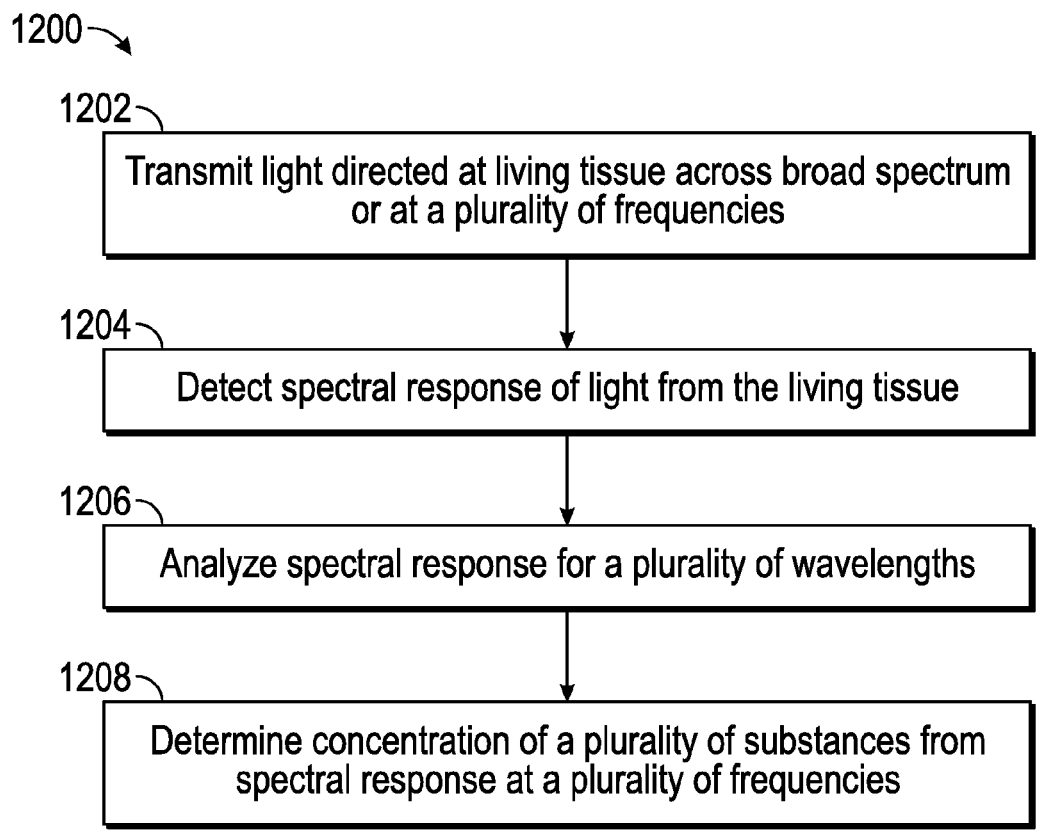
FIG. 12 illustrates a logical flow diagram of an exemplary method to determine blood concentration levels of a plurality of substances using the spectral response for a plurality of wavelengths.

FIG. 12 illustrates a logical flow diagram of an exemplary method 1200 to determine blood concentration levels of a plurality of substances using the spectral response for a plurality of wavelengths. The biosensor 100 transmits light directed at living tissue. The light may be across a broad spectrum or at a plurality of discrete frequencies or at a single frequency. For example, the light may be emitted using a broad spectrum light source or multiple LEDs transmitting at discrete wavelengths or a tunable laser transmitting at one or more frequencies. The spectral response of light (e.g. either transmitted through the living tissue or reflected by the living tissue) is detected at 1204. The spectral response is analyzed at a plurality of wavelengths (and ranges of +/−20 to 50 nm around these wavelengths) at 1206. In one aspect, the systolic and diastolic points are determined at the plurality of wavelengths and the L values are calculated using the systolic and diastolic points. In one aspect, the L values are determined at incremental wavelengths, such as at 1 nm or 1.5 nm or 2 nm incremental wavelengths. In another aspect, the L values are calculated for a set of predetermined wavelengths. A ratio R value may also be determined using L values derived from a first spectral response obtained for a first wavelength (and in one aspect including a range of +/−20 to 50 nm) and a spectral response obtained for a second wavelength (and in one aspect including a ranges of +/−20 to 50 nm).

Using the absorption coefficients associated with the plurality of substances, the concentration levels of a plurality of substances may then be determined. For example, the intensity of light may be due to absorption by a plurality of substances in the arterial blood flow. For example, $$LN(I_{1-n}) = \mu_1 * C_1 + \mu_2 * C_2 + \mu_3 * C_3 \ldots + \mu_n * C_n$$

wherein, $I_{1-n}$=intensity of light at wavelengths $\lambda_{1-n}$ $\mu_n$=absorption coefficient of substance 1, 2, ... n at wavelengths $\lambda_{1-n}$ $C_n$=Concentration level of substance 1, 2, ... n When the absorption coefficients $\mu_{1-n}$ are known at the wavelengths $\lambda_{1-n}$, then the concentration levels $C_{1-n}$ of multiple substances may be determined.

Figure 13:
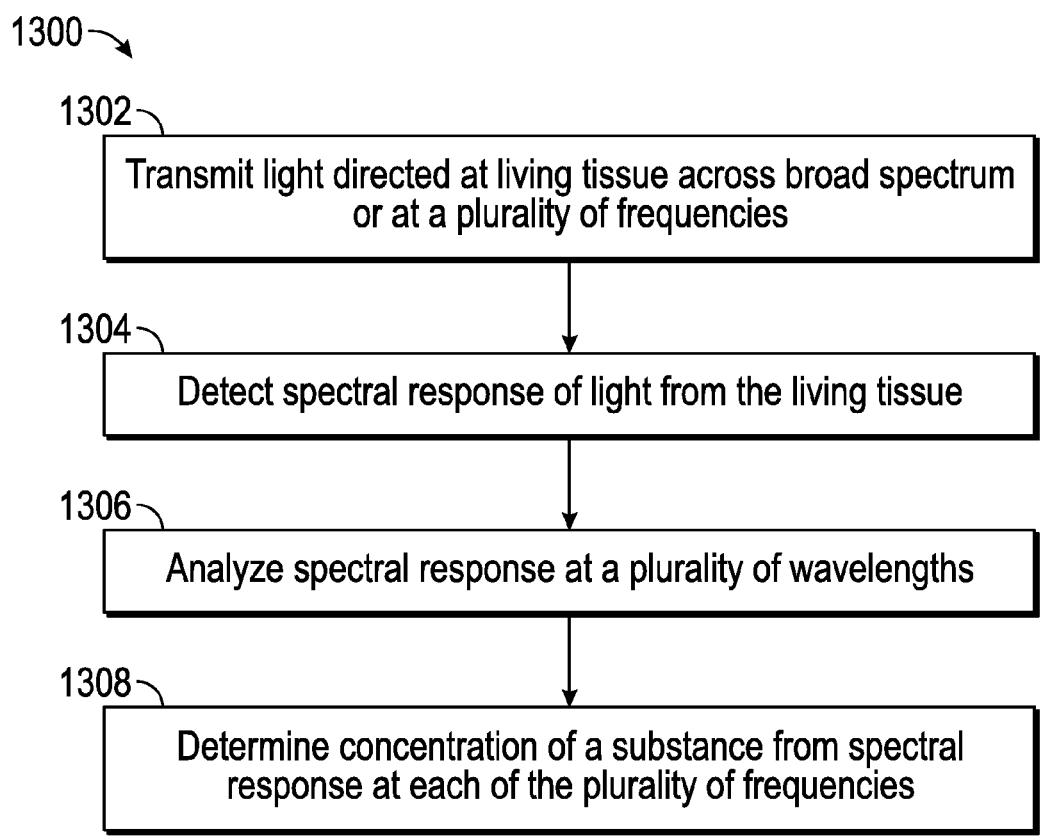
FIG. 13 illustrates a logical flow diagram of an exemplary method to determine blood concentration levels of a single substance using the spectral response for a plurality of wavelengths.

FIG. 13 illustrates a logical flow diagram of an exemplary method 1300 to determine blood concentration levels of a single substance using the spectral response for a plurality of wavelengths. The intensity of light at a plurality of wavelengths may be due to absorption by a single substance in the arterial blood flow. For example, a single substance may absorb or reflect a plurality of different wavelengths of light. In this example then, $$LN(I_{1-n}) = \mu_1 * C + \mu_2 * C + \mu_3 * C \ldots + \mu_n * C$$

wherein, $I_{1-n}$=intensity of light at wavelengths $\lambda_1$, $\mu_n$=absorption coefficient of a substance at wavelengths $\lambda_{1-n}$ C=Concentration level of a substance When the absorption coefficients $\mu_{1-n}$ of the single substance are known at the wavelengths $\lambda_{1-n}$, then the concentration level C of the substance may be determined from the spectral response for each of the wavelengths (and in one aspect including a range of 1 nm to 50 nm around each of the wavelengths). Using the spectral response at multiple frequencies provides a more robust determination of the concentration level of the substance.

Figure 14:
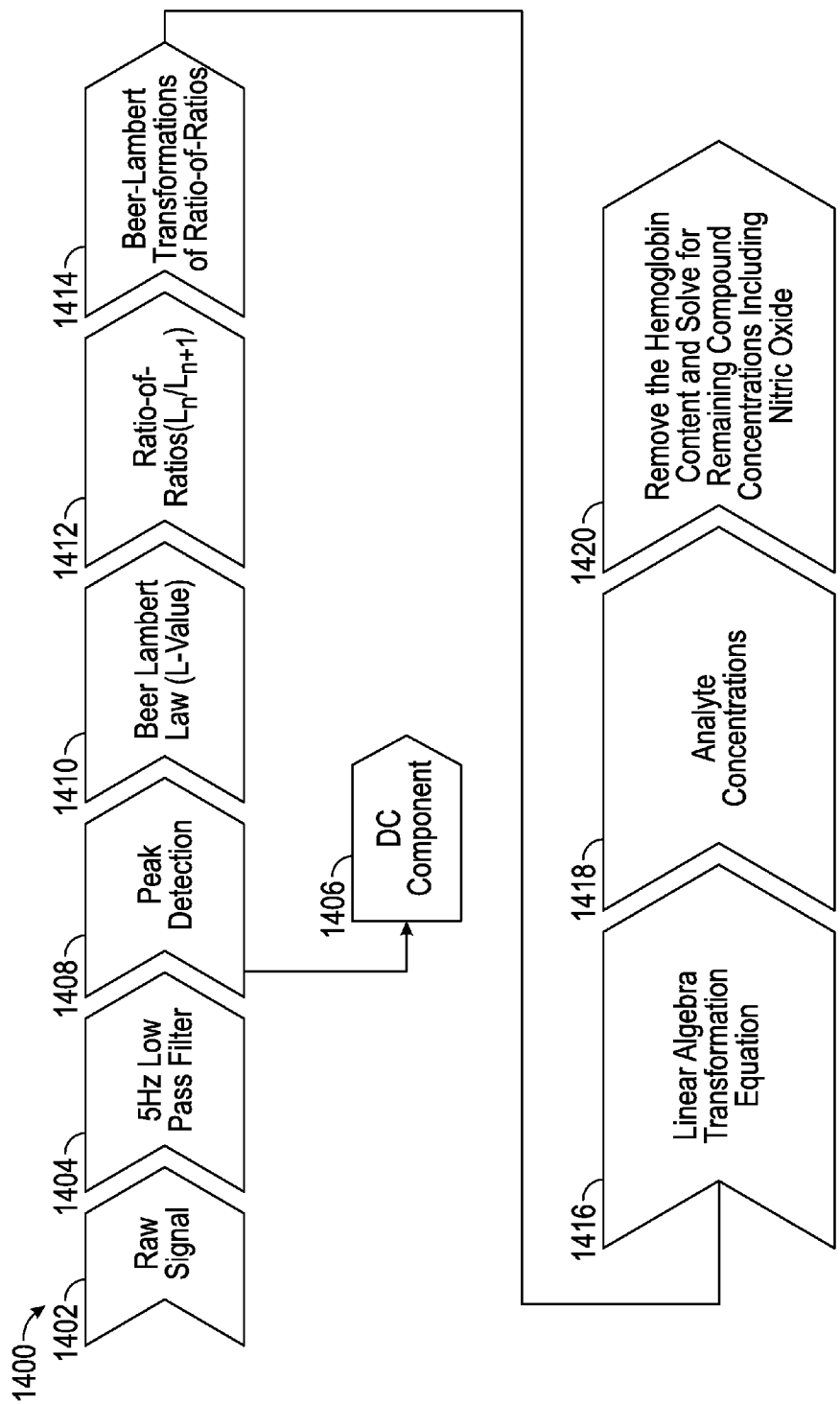
FIG. 14 illustrates a schematic block diagram of an embodiment of a method 1400 for determining concentration levels or indicators of substances in pulsating blood flow in more detail.

In use, the biosensor 100 transmits light directed at living tissue at a plurality of discrete wavelengths or over a broad spectrum at 1302. The spectral response of light from the living tissue is detected at 1304, and the spectral response is analyzed for a plurality of wavelengths (and in one aspect including a range of +/−20 to 50 nm around each of the wavelengths) at 1306. Then, the concentration level C of the substance may be determined from the spectral response for each of the plurality of wavelengths at 1308. An example for calculating the concentration of one or more substances over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, ... n at wavelengths $\lambda_{1-n}$ $C_n$=Concentration level of substance 1, 2, ... n FIG. 14 illustrates a schematic block diagram of an embodiment of a method 1400 for determining concentration levels or indicators of substances in pulsating blood flow in more detail. The biosensor 100 obtains a spectral response signal at a first wavelength and at a second wavelength at 1402. The spectral response signal includes AC and DC components IAC+DC. A low pass filter is applied to the spectral response signal IAC+DC to isolate the DC component 1406 of the spectral response signal at each wavelength at 1404. The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 1408. The systolic and diastolic measurements are compared in order to compute the L values using Beer-Lambert equations at 1410. For example, a logarithmic function may be applied to the ratio of IAC+DC and IDC to obtain an L value for the first wavelength LλJ and for the second wavelength Lλ2. The ratio R of the first wavelength LλJ and for the second wavelength Lλ2 may then be calculated at 1412. When multiple frequencies are used to determine a concentration level of one or more substances, the the linear function described herein are applied at 1416, and the one or more concentration levels of the substances or analytes are determined at 1418.

In an embodiment, a substances or analyte may be attached in the blood stream to one or more hemoglobin compounds. The concentration level of the hemoglobin compounds may then need to be subtracted from the concentration level of the substance to isolate the concentration level of the substance from the hemoglobin compounds. For example, nitric oxide (NO) is found in the blood stream in a gaseous form and also attached to hemoglobin compounds. Thus, the measurements at $L_{390\ nm}$ to detect nitric oxide may include a concentration level of the hemoglobin compounds as well as nitric oxide.

The hemoglobin compound concentration levels may be determined and subtracted to isolate the concentration level of the substance at 1420. The hemoglobin compounds include, e.g., Oxyhemoglobin [HbO2], Carboxyhemoglobin [HbCO], Methemoglobin [HbMet], and reduced hemoglobin fractions [RHb]. The biosensor 100 may control the PPG circuit 110 to detect the total concentration of the hemoglobin compounds using a center frequency of 660 nm and a range of 1 nm to 50 nm. A method for determining the relative concentration or composition of different kinds of hemoglobin contained in blood is described in more detail in U.S. Pat. No. 6,104,938 issued on Aug. 15, 2000, which is hereby incorporated by reference herein.

Various unexpected results were determined from clinical trials using the biosensor 100. In one aspect, based on the clinical trials, an R value obtained from the ratio $L_{\lambda 1=390\ nm}$/and $L_{\lambda 2=940}$ was found to be a predictor or indicator of diabetic risk or diabetes as described in more detail herein. In another aspect, based on the clinical trials, the R value obtained from the ratio of $L_{468\ nm}/L_{940\ nm}$, was identified as an indicator of the liver enzyme marker, e.g. P450. In another aspect, based on the clinical trials, the R value obtained from the ratio of $L_{592\ nm}/L_{940\ nm}$, was identified as an indicator of digestion phases, such as phase 1 and phase 2, in the arterial blood flow. In another aspect, the R value from the ratio of $L_{660\ nm}/L_{940\ nm}$, was found to be an indicator of oxygen saturation levels $SpO_2$ in the arterial blood flow. In another aspect, it was determined that the biosensor 100 may determine alcohol levels in the blood using spectral responses for wavelengths at 390 and/or 468 nm. In general, the second wavelength of 940 nm is selected because it has a low absorption coefficient for the targeted substances described herein. Thus, another wavelength other than 940 nm with a low absorption coefficient for the targeted substances (e.g. at least less than 25% of the absorption coefficient of the targeted substance for the first wavelength) may be used instead. For example, the second wavelength of 940 nm may be replaced with 860 nm that has a low absorption coefficient for the targeted substances. In another aspect, the second wavelength of 940 nm may be replaced with other wavelengths, e.g. in the IR range, that have a low absorption coefficient for the targeted substances. In general, it is desired that the spectral response for the first predetermined wavelength have a higher intensity level than the spectral response for the second predetermined wavelength.

In another aspect, it was determined that other proteins or compounds, such as those present or with higher concentrations in the blood with persons having cancer, may be detected using similar PPG techniques described herein with biosensor 100 at one or more other wavelengths. Cancer risk may then be determined using non-invasive testing over a short measurement period of 1-10 minutes. Since the biosensor may operate in multiple frequencies, various health monitoring tests may be performed concurrently. For example, the biosensor 100 may measure for diabetic risk, liver enzymes, alcohol levels, cancer risk or presence of other analytes within a same measurement period using PPG techniques.

Figure 15:
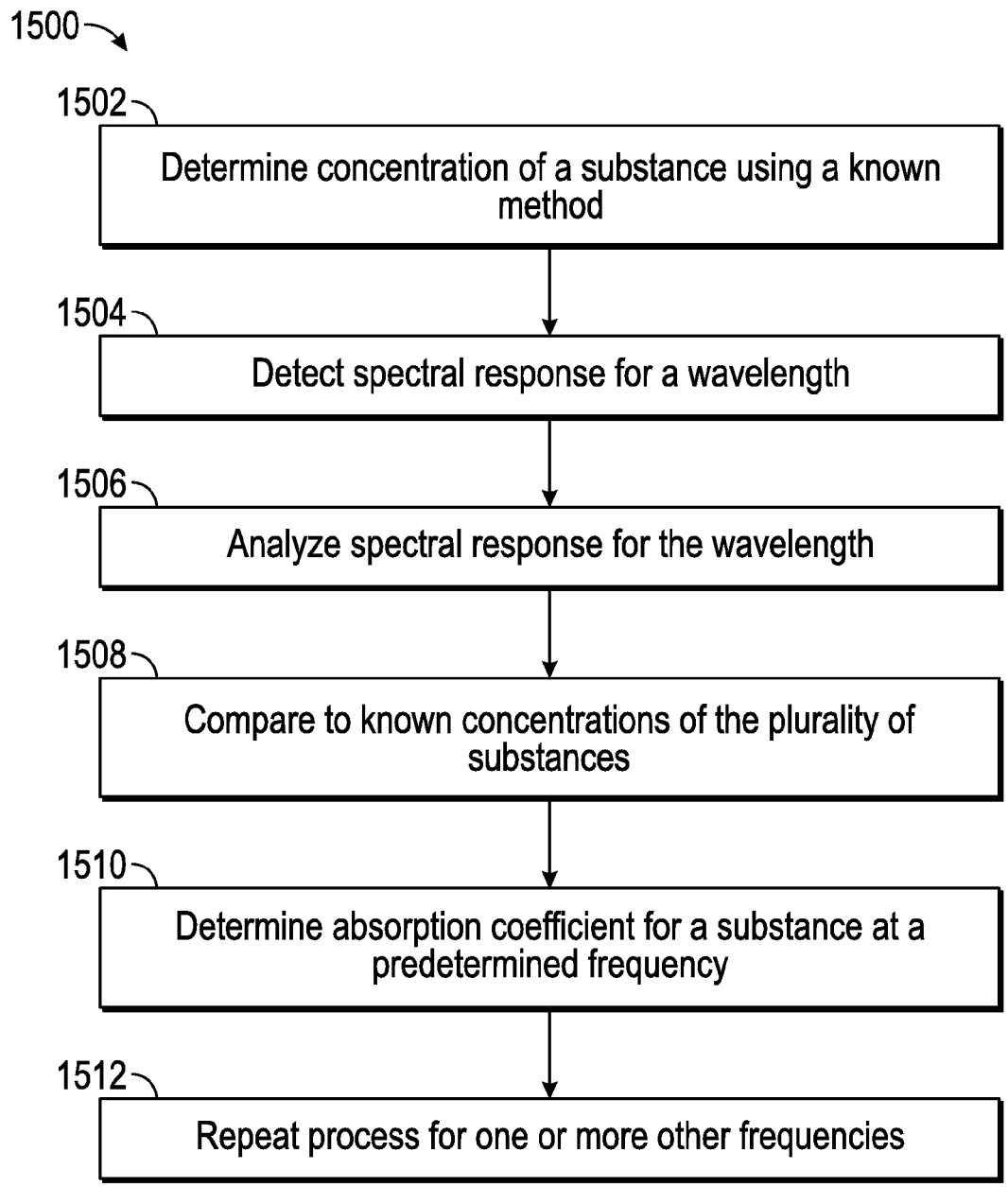
FIG. 15 illustrates a logical flow diagram of an exemplary method to determine an absorption coefficients $\mu$ of a substance at a wavelength $\lambda$.

FIG. 15 illustrates a logical flow diagram of an exemplary method 1500 to determine an absorption coefficients μ of a substance at a wavelength λ. The concentration level of a substance in arterial blood is obtained using a known method at 1502. For example, blood may be extracted at predetermined intervals during a time period and a blood gas analyzer may be used to measure a concentration level of a substance. The biosensor 100 emits light at a wavelength (and in one aspect for a range of 1 nm-50 nm around the wavelength) and detects a spectral response for the wavelength (and in one aspect for a range of 1 nm-50 nm around the wavelength). The spectral response for the predetermined wavelength is analyzed at 1506. The intensity of the detected light is determined. The intensity of the detected light is compared to the known concentration level of the substance at 1508. The absorption coefficient for the substance may then be determined using the Beer-Lambert equations described herein at 1510.

The above process may be repeated at one or more other frequencies at 1512. For example, as described herein, the spectral analysis over a range or at multiple frequencies may be analyzed to determine one or more frequencies with a higher intensity or power level in response to a concentration level or presence of the substance. Thus, one or more frequencies may be analyzed and identified for detection of the substance, and the absorption coefficient for the substance determined at the one or more frequencies.

In another embodiment, the concentration level of a substance may be obtained from predetermined values obtained through experimentation. For example, in a calibration phase, a correlation table may be compiled through experimentation that includes light intensity values $I_{1-n}$ at one or more wavelengths $\lambda_{1-n}$ and a corresponding known concentration level for the substance for the light intensity values. In use, the biosensor 100 detects a spectral response and determines the light intensity values $I_{1-n}$ at one or more wavelengths $\lambda_{1-n}$. The biosensor 100 then looks up the detected light intensity values $I_{1-n}$ in the correlation table to determine the concentration level of the substance.

Embodiment—Biosensor Form Factors

Figure 16A:
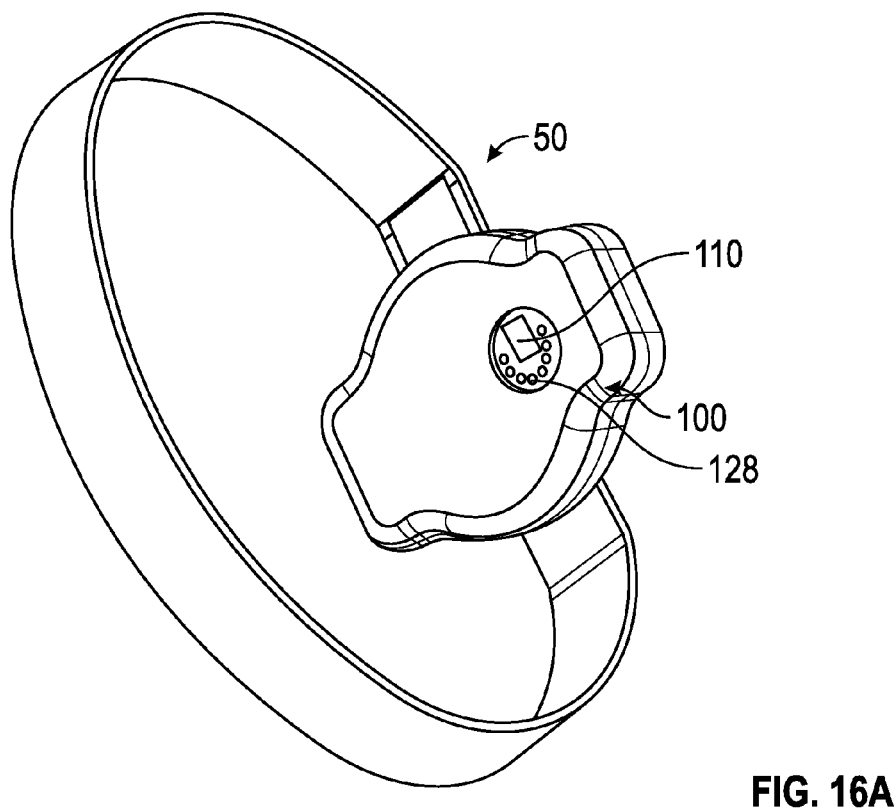
FIG. 16A and FIG. 16B illustrate perspective views of another embodiment of the health care band.
Figure 16B:
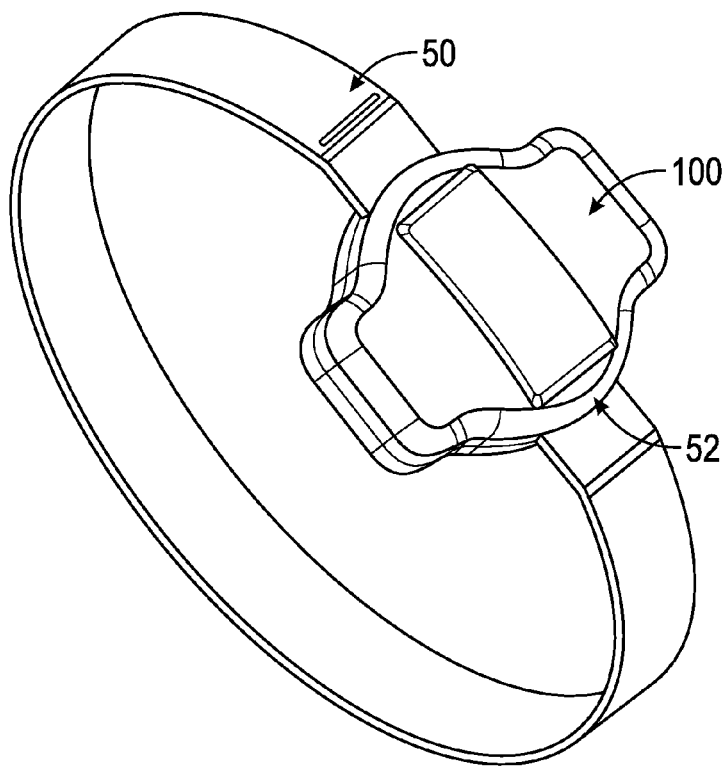

FIG. 16A and FIG. 16B illustrate perspective views of another embodiment of the health care band 50. The health care band 50 may be adjustable to varying circumferences. The biosensor 100 may be detachable from the health care band 50. In one aspect, the biosensor 100 is removeably attached to the health care band 50 using an attachment mechanism 52. For example, the attachment mechanism 52 may include clips or a holder that the band slides through or other means for attachment and detachment of the biosensor 100 to the health care band 50.

For example, during MRI tests, the biosensor 100 may need to be detached from the health care band 50 to minimize metallic substances in the MRI device. The biosensor 100 may then be reattached to the health care band using the attachment mechanism 52 after the MRI test. In another example, the health care band 50 may need to be replaced if damaged or torn. The biosensor 100 may be detached from the damaged band and reattached to a new band. The health care band may be disposable and unique to each patient. The health care band 50 may be configured with an adjustable band for placement or attachment to the patient on an arm, on one or more fingers, around a leg, etc. In general, the arm band should be secured such that the aperture of the PPG circuit 110 of the biosensor 100 is positioned against or adjacent to or facing the skin of the patient.

Upon admission, a biosensor 100 is programmed with a patient identification that is associated with a patient's EMR. The biosensor is attached to the patient using the health care band 50. The biosensor 100 may then immediately begin to measure a patient's vitals, such as heart rate, pulse, blood oxygen levels, blood glucose or insulin levels, etc. The patient's vitals are then monitored continuously by the biosensor 100 on the armband without further manual intervention or additional instruments. The biosensor may be used to track progress throughout the patient care chain and provide medical alerts to notify when vitals are critical or reach a certain predetermined threshold. The biosensor 100 transmits the data measurements to the EMR network for inclusion in the patient's EMR as well as to a monitoring station, another hospital or physician's office, etc.

Figure 17A:
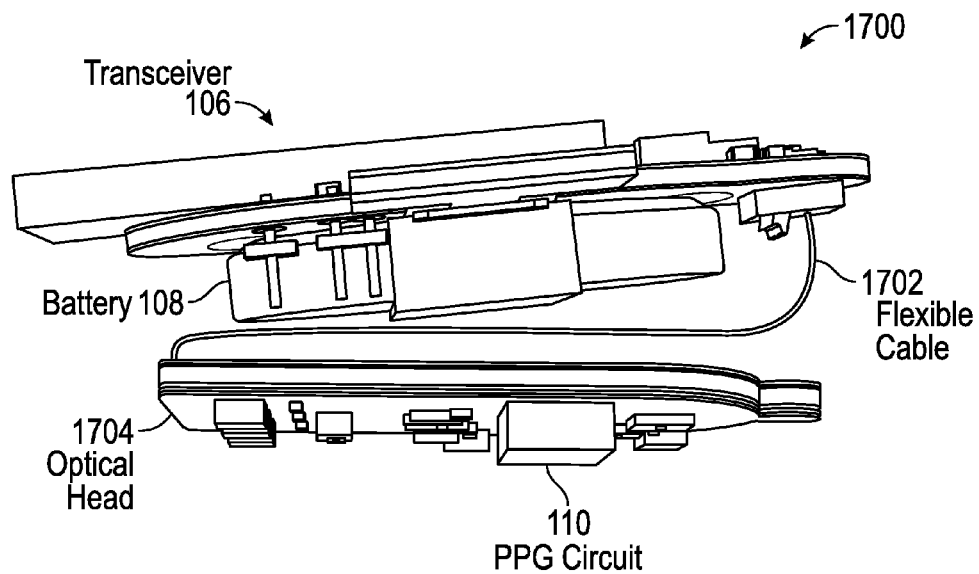
FIG. 17A illustrates an exemplary embodiment of another form factor of the biosensor.

FIG. 17A illustrates an exemplary embodiment of another form factor of the biosensor 100. In an embodiment, the biosensor 100 is implemented on a wearable patch 1700. The wearable patch 1700 may include an adhesive backing to attach to a skin surface of a patient, such as on a hand, arm, wrist, forehead, chest, abdominal area, or other area of the skin or body or living tissue. Alternatively, the wearable patch 1700 may be attached to the skin surface using adhesive tape. A flexible cable 1702 may be used to attach an optical head 1704 of the wearable patch 1700 to the other components of the biosensor 100, such as the wireless transceiver 106 and battery 108. Thus, during a magnetic resonance imaging (MRI) test when metal needs to be minimal, the battery 108 and transceiver 106 may be temporarily removed. In addition, the flexible cable 1702 may be used to open the biosensor 100 to replace the battery 108.

Figure 17B:
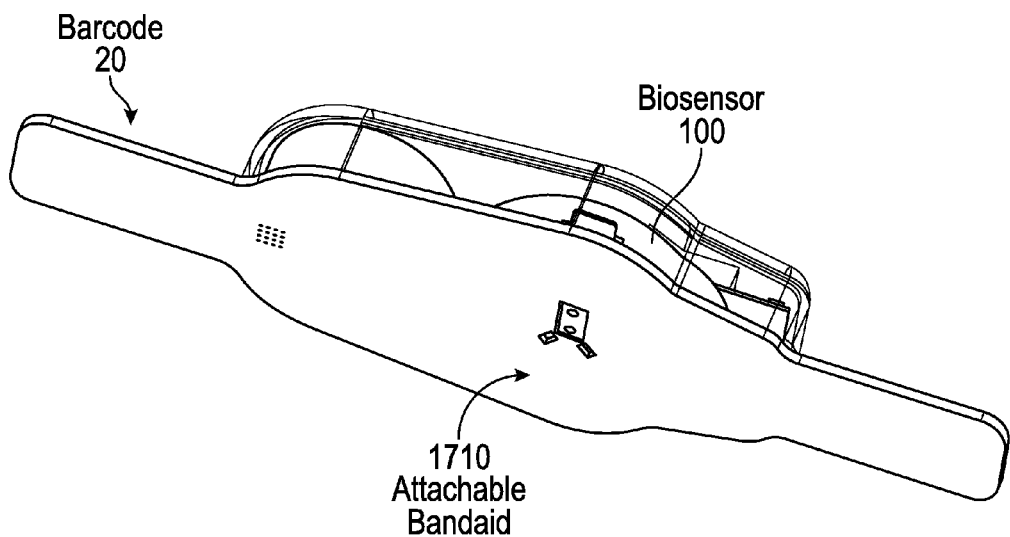
FIG. 17B illustrates an exemplary embodiment of another form factor of the biosensor.

FIG. 17B illustrates an exemplary embodiment of another form factor of the biosensor 100. In this embodiment, the biosensor 100 may be coupled to an attachable bandaid 1710. The attachable bandaid 1710 may be attached via adhesive or adhesive tape to a skin surface of the patient, e.g. finger, forehead, arm, stomach, leg, wrist, etc.

Figure 18:
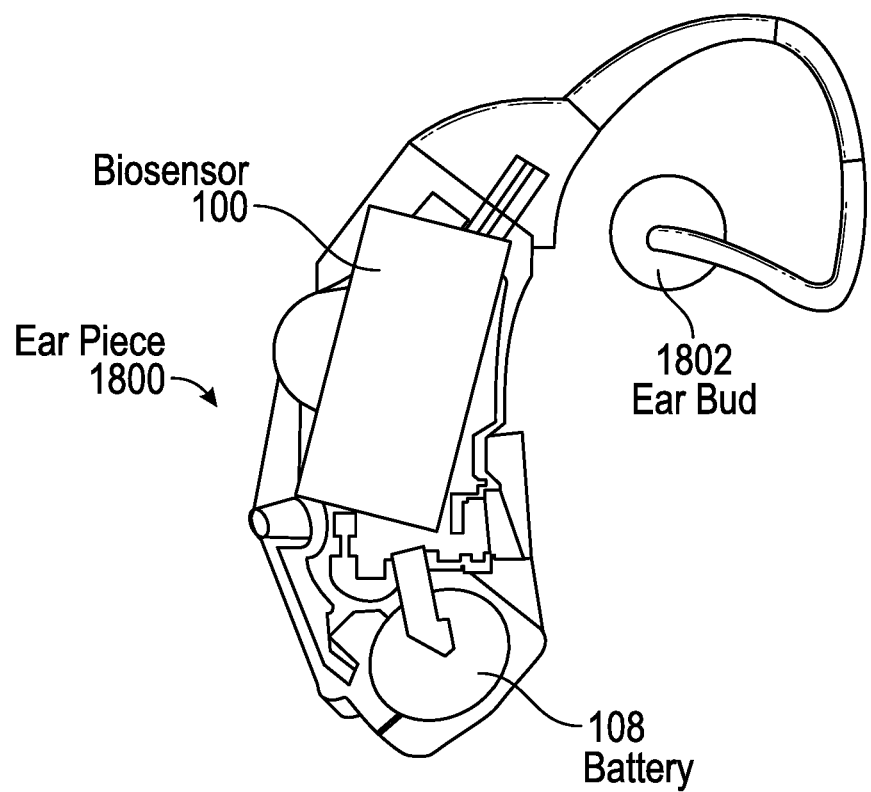
FIG. 18 illustrates an exemplary embodiment of another form factor of the biosensor.

FIG. 18 illustrates an exemplary embodiment of another form factor of the biosensor 100. In this embodiment, the biosensor 100 is configured in an earpiece 1800. The earpiece 1800 includes an earbud 1802. The biosensor 100 is configured to transmit light into the ear canal from one or more optical fibers 152 in the ear bud 1802 and detect light from the ear canal using the one or more optical fibers 152.

Figure 19A:
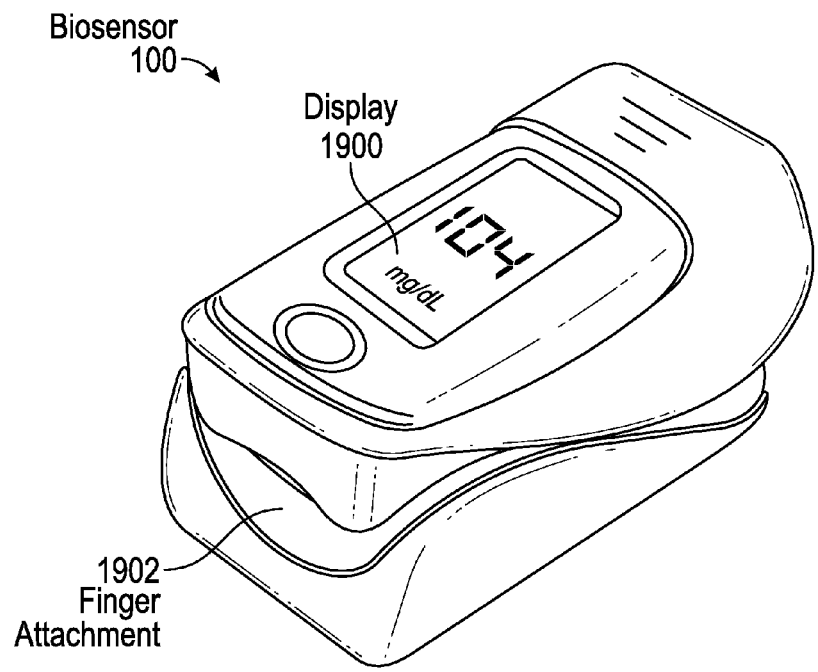
FIG. 19A illustrates an exemplary embodiment of another form factor of the biosensor.

FIG. 19A illustrates an exemplary embodiment of another form factor of the biosensor 100. In this embodiment, the biosensor 100 is configured to attach to a finger or fingertip using finger attachment 1902. The finger attachment 1902 is configured to securely hold a finger that is inserted into the finger attachment 1902. A display 1900 is implemented on the biosensor 100 with a graphical user interface (GUI) that displays biosensor data. For example, in use, the biosensor 100 measures blood glucose levels using the PPG circuit 110. The blood glucose levels are then displayed using the GUI on the display 1900. The PPG circuit may also measure other patient vitals that are displayed on the display 1900, such as oxygen saturation levels, temperature, respiration rates, heart rate, blood alcohol levels, digestive response, caloric intake, white blood cell count, electrolyte or other blood analyte concentrations, liver enzymes, etc. The biosensor 100 may thus provide biosensor data continuously and non-invasively.

Figure 19B:
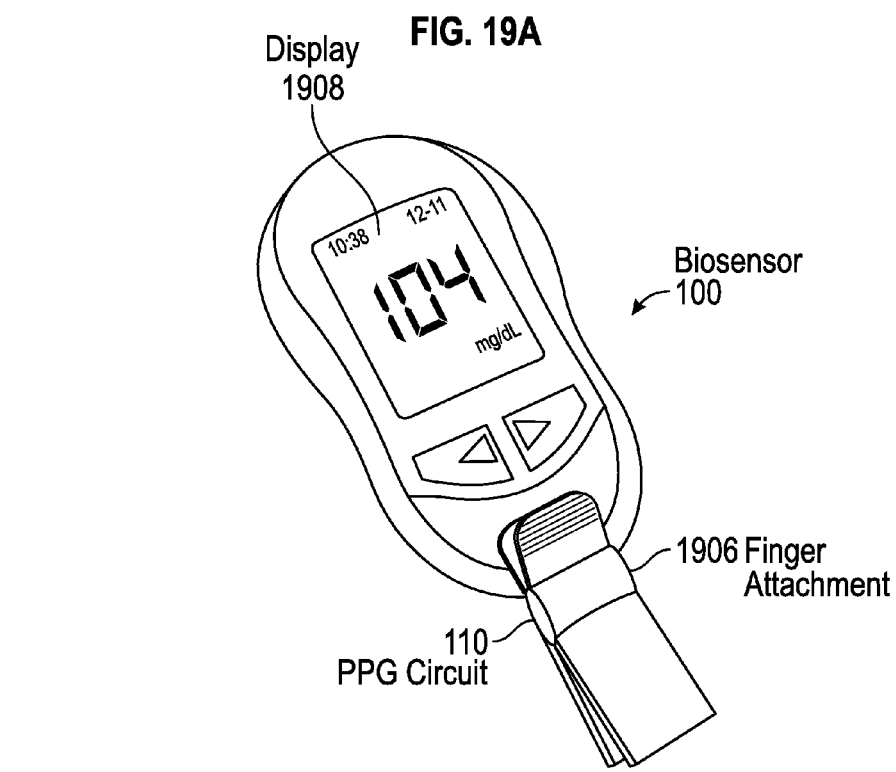
FIG. 19B illustrates an exemplary embodiment of another form factor of the biosensor.

FIG. 19B illustrates an exemplary embodiment of another form factor of the biosensor 100. In this embodiment, the biosensor 100 is configured to attach to a finger or fingertip using finger attachment 1906. The finger attachment 1906 includes the PPG circuit 110 and is configured to securely hold a finger that is inserted into the finger attachment 1906. The finger attachment 1906 may be implemented within the same encasement as the other components of the biosensor 100 or be communicatively coupled either through a wired or wireless interface to the other components of the biosensor 100. A display 1908 is implemented for the biosensor 100 with a graphical user interface (GUI) that displays biosensor data including blood glucose levels.

The biosensor 100 may be configured to be attached to an ear lobe or other body parts in other form factors. In addition, one or more biosensors 100 in one or more form factors may be used in combination to determine biosensor data at one or more areas of the body.

In these or other form factors, the biosensor 100 may store the unique patient identification 172 that is generally included as a barcode on current armbands. The biosensor 100 may also store biosensor data measured by the biosensor 100 or EMR 170 of the patient that may be used in one or more applications or systems in the health care chain of a patient. For example, the biosensor 100 is programmed with a unique patient identification 172 that is assigned to a patient during admission to a hospital and is used for tracking of the patient through the transceiver 106 of the biosensor 100. As such, a separate scanner is not needed to track a patient or scan an arm band. The biosensor 100 monitors the patient's vitals as part of the care management of the patient. The patients vitals are used in data analytics for diagnosis, treatment options, monitoring, etc. The patient vitals may be included in the patient EMR 170 and otherwise used for patient health. The biosensor 100 may also communicate with inventory management. For example, when a medicine is provided to a patient, this information of the medicine and dosage may be provided to the inventory management system. The inventory management system is then able to adjust the inventory of the medicine. The biosensor 100 may thus have these and/or additional applications.

Embodiment—EMR Network

Figure 20:
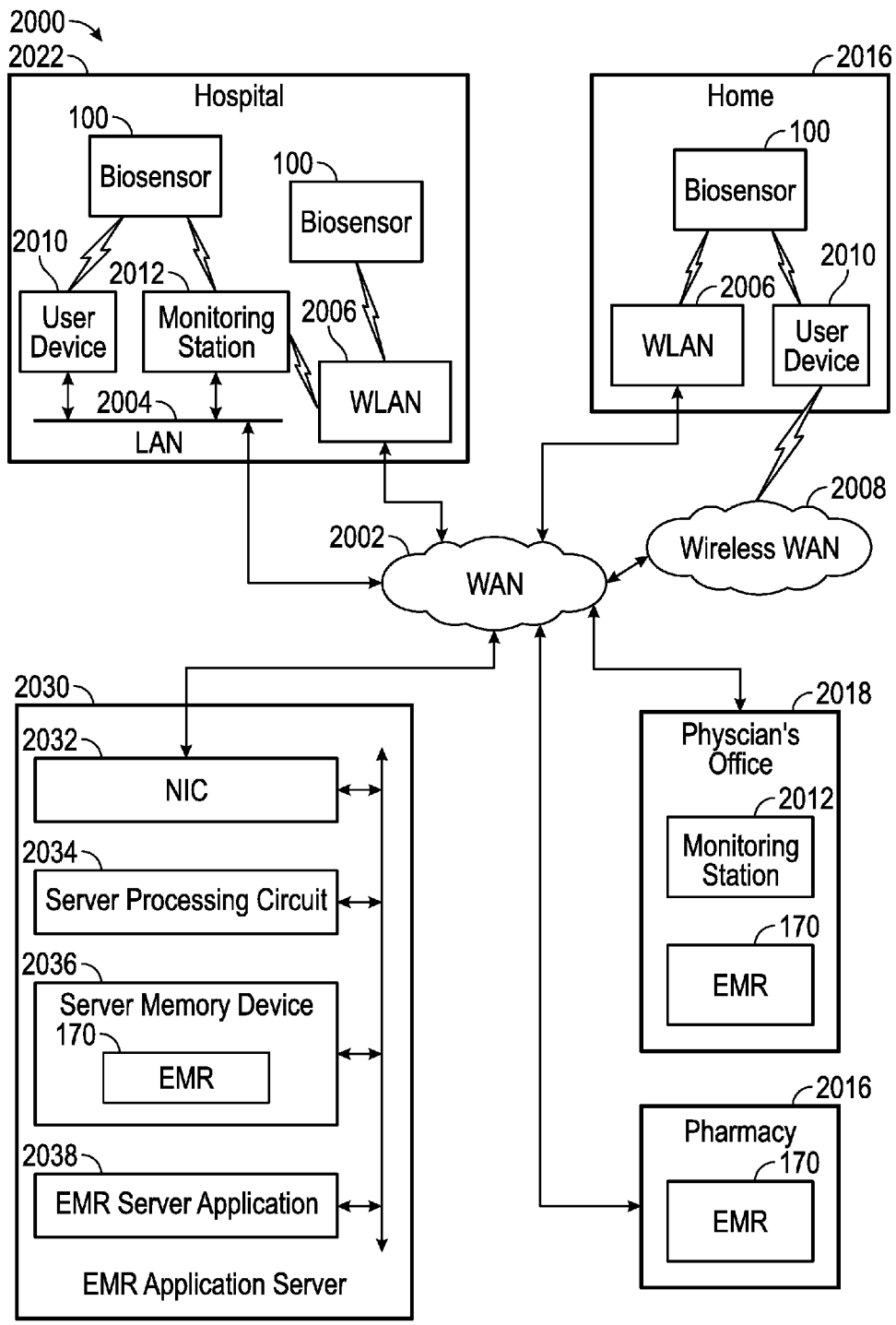
FIG. 20 illustrates a schematic block diagram of an embodiment of an exemplary network in which the biosensor described herein may operate.

FIG. 20 illustrates a schematic block diagram of an embodiment of an exemplary network 2000 in which the biosensor 100 described herein may operate. The exemplary network 2000 may include a combination of one or more networks that are communicatively coupled, e.g., such as a wide area network (WAN) 2002, a wired local area network (LAN) 2004, a wireless local area network (WLAN) 2006, or a wireless wide area network (WAN) 2008. The wireless WAN 1228 may include, for example, a 3G or 4G cellular network, a GSM network, a WIMAX network, an EDGE network, a GERAN network, etc. or a satellite network or a combination thereof. The WAN 1222 includes the Internet, service provider network, other type of WAN, or a combination of one or more thereof. The LAN 2004 and the WLANs 20066 may operate inside a home 2016 or enterprise environment, such as a physician's office 2018, pharmacy 2020 or hospital 2022 or other caregiver.

The biosensor 100 may communicate to one or more user devices 2010, such as a smart phone, laptop, desktop, smart tablet, smart watch, or any other electronic device that includes a display for illustrating the patient's vitals. In one aspect, the user device 2010 or biosensor 100 may communicate the patient's vitals to a local or remote monitoring station 2012 of a caregiver or physician.

One or more biosensor 100s are communicatively coupled to an EMR application server 2030 through one or more of user devices and/or the exemplary networks in the EMR network 2000. The EMR server 2030 includes a network interface card (NIC) 2032, a server processing circuit 2034, a server memory device 2036 and EMR server application 2038. The network interface circuit (NIC) 1202 includes an interface for wireless and/or wired network communications with one or more of the exemplary networks in the EMR network 1220. The network interface circuit 1202 may also include authentication capability that provides authentication prior to allowing access to some or all of the resources of the EMR application server 1200. The network interface circuit 1202 may also include firewall, gateway and proxy server functions.

One or more of the biosensors 100 are communicatively coupled to an EMR application server 1200 through one or more of the exemplary networks in the EMR network 1220. The EMR application server 1200 includes a network interface circuit 1202 and a server processing circuit 1204. The network interface circuit (NIC) 1202 includes an interface for wireless and/or wired network communications with one or more of the exemplary networks in the EMR network 1220. The network interface circuit 1202 may also include authentication capability that provides authentication prior to allowing access to some or all of the resources of the EMR application server 1200. The network interface circuit 1202 may also include firewall, gateway and proxy server functions.

The EMR application server 1200 also includes a server processing circuit 2034 and a memory device 2036. For example, the memory device 2036 is a non-transitory, processor readable medium that stores instructions which when executed by the server processing circuit 2034, causes the server processing circuit 2034 to perform one or more functions described herein. In an embodiment, the memory device 2036 stores a patient EMR 170 that includes biosensor data and historical data of a patient associated with the patient ID 172.

The EMR application server 1200 includes an EMR server application 2038. The EMR server application 2038 is operable to communicate with the biosensors 100 and/or user devices 2010 and monitoring stations 2012. The EMR server application 2038 may be a web-based application supported by the EMR application server 2030. For example, the EMR application server 2030 may be a web server and support the EMR server application 2038 via a website. In another embodiment, the EMR server application 2038 is a stand-alone application that is downloaded to the user devices 2010 by the EMR application server 2030 and is operable on the user devices 2010 without access to the EMR application server 2030 or only needs to accesses the EMR application server 2030 for additional information and updates.

In use, the biosensors 100 may communicate patient's biosensor data to the EMR application server 2030. A biosensor 100 may be programmed with a patient identification 172 that is associated with a patient's EMR 170. The biosensor 100 measures the patient's vitals, such as heart rate, pulse, blood oxygen levels, blood glucose levels, etc. and may also control an integrated or separate drug delivery system to administer medications to the patient. The biosensor 100 is configured to transmit the patient vitals to the EMR application server 2030. The EMR server application 2038 updates an EMR 170 associated with the patient identification 172 with the patient vitals.

The EMR application server 2030 may also be operable to communicate with a physician's office 2018 or pharmacy 2016 or other third party health care provider over the EMR network 2000 to provide biosensor data and receive instructions on dosages of medication. For example, the EMR server application 2038 may transmit glucose level information, heart rate information or pulse rate information or medication dosages or blood concentration levels of one or more relevant substances to a physician's office 2018. The EMR server application 2038 may also be configured to provide medical alerts to notify a user, physician or other caregiver when vitals are critical or reach a certain predetermined threshold.

The EMR server application 1408 may also receive instructions from a doctor's office, pharmacy 2016 or hospital 2022 or other caregiver regarding a prescription or administration of a dosage of medication. The EMR server application 2038 may then transmit the instructions to the biosensor 100. The instructions may include a dosage amount, rate of administration or frequency of dosages of a medication. The biosensor 100 may then control a drug delivery system to administer the medication automatically as per the transmitted instructions.

Embodiment—Interoperability of Biosensors and Other Devices

Figure 21A:
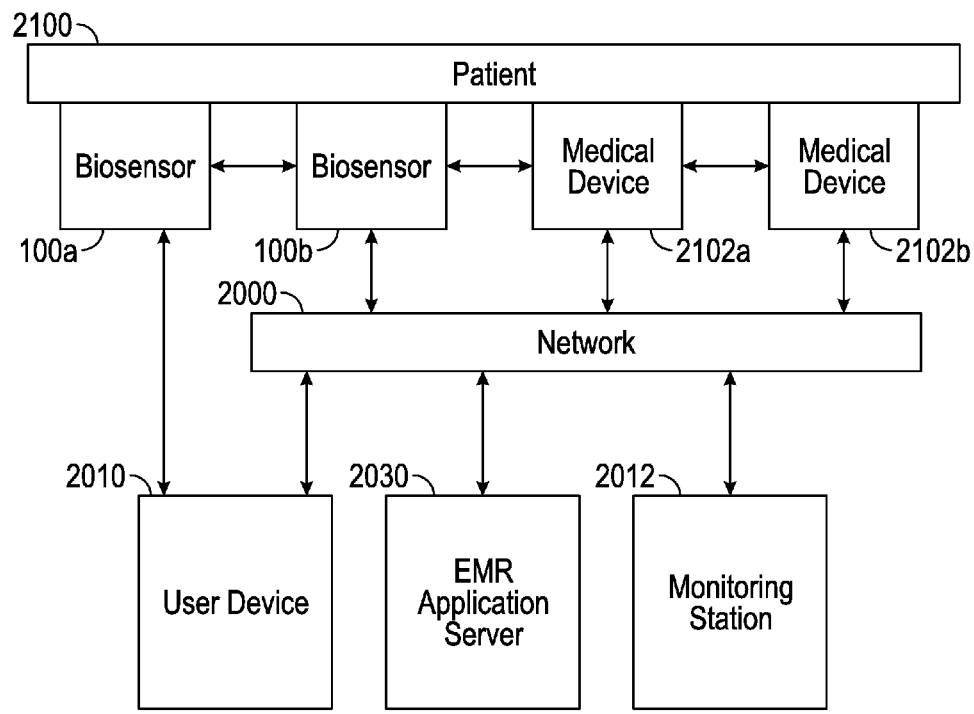
FIG. 21A illustrates a schematic block diagram of an embodiment of a network illustrating interoperability of a plurality of bio sensors.

FIG. 21A illustrates a schematic block diagram of an embodiment of a network illustrating interoperability of a plurality of biosensors 100. A plurality of biosensors 100 may interface with a patient and communicate with one or more of the other biosensor 100s. The biosensors 100 may communicate directly or communicate indirectly through a WLAN or other type of network as illustrated in the Network 2000 of FIG. 20. For example, a first biosensor 100a may include a PPG circuit 110 configured to detect a blood glucose level. For better detection, the biosensor 100a is positioned on a wrist. A second biosensor 100b may include a drug delivery system 116 configured to administer insulin to the patient 2100 and is positioned on an abdominal area of the patient 2100. In use, the first biosensor 100a continuously monitors blood glucose levels and then communicates either directly or indirectly the detected levels to the second biosensor 100b. The second biosensor 100b then administers a dosage of insulin at an administration rate and/or frequency rate in response to the detected blood glucose levels.

In another example, one or more biosensor 100s may communicate directly or indirectly with one or more other types of medical devices 2102 interfacing with a same patient, such as a first medical device 2100a and a second medical device 2100b. The first medical device 2102a may include an insulin pump, e.g. on body insulin pump or catheter tethered drip system. In use, the biosensor 100a monitors glucose and/or insulin indicators or concentration levels in the patient using the PPG circuit 110. In response to the detected glucose and/or insulin concentration/indicators, the biosensor 100a communicates either directly or indirectly administration instructions to the first medical device 2102a. The administration instructions may include dosage amount, administration rate and/or frequency rate. In response to the administration instructions, the first medical device 2102a administers an insulin infusion to the patient. The first biosensor 100a may continuously monitor glucose/insulin indicators or concentration levels and provide automatic instructions to the first medical device 2102a for the administration of insulin.

In another example, a plurality of biosensors 100, such as the first biosensor 100a and the second biosensor 100b, may be positioned on a patient to monitor an ECG of the patient. The biosensors 100 may communicate the ECG measurements directly or indirectly to each other to generate an electrocardiogram. The electrocardiogram is transmitted to an EMR application server 2030 or monitoring station 2012 or to a user device 2010. Based on the electrocardiogram, a doctor or user may provide instructions to the second medical device 2102b. For example, the second medical device 2102b may include a Pacemaker or drug delivery system.

In another example, the biosensor 100a may include a PPG circuit 110 configured to detect alcohol levels in arterial blood flow. The user device 2010 may include a locking system installed in an ignition system of a vehicle. In order to start the vehicle, the biosensor 100a detects the blood alcohol concentration (BAC) of the patient. Then the biosensor 100a determines whether the blood alcohol concentration (BAC) is above or below a preset legal limit. If it is below this limit, the biosensor 100a communicates an instruction to the user device 2010 to unlock the ignition to allow starting of the vehicle. If it is above the limit, the biosensor 100a instructs the user device 2010 to lock the ignition to prevent starting of the vehicle. Since the biosensor 100a is directly testing the blood alcohol levels, the biosensor 100a may be more accurate and convenient than current breathe analyzers.

Embodiment—Adjustments in Response to Positioning of the Biosensor

Figure 21B:
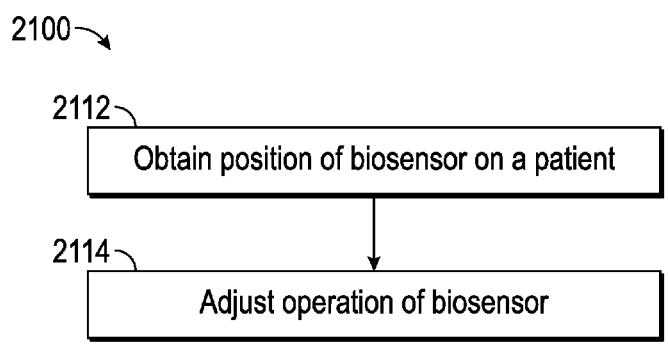
FIG. 21B illustrates a logical flow diagram of an embodiment of a method for adjusting operation of the biosensor in response to a position of the biosensor.

FIG. 21B illustrates a logical flow diagram of an embodiment of a method 2110 for adjusting operation of the biosensor 100 in response to a position of the biosensor 100. The biosensor 100 may be positioned on different parts of a patient that exhibit different characteristics. For example, the biosensor 100 may be positioned on or attached to various areas of the body, e.g. a hand, a wrist, an arm, forehead, chest, abdominal area, ear lobe, fingertip or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of underlying tissue.

The biosensor 100 is configured to obtain position information on a patient at 2112. The position information may be input from a user interface. In another aspect, the biosensor 100 may determine its positioning, e.g. using the activity monitoring circuit 114 and/or PPG circuit 110. For example, the PPG circuit 110 may be configured to detect characteristics of underlying tissue. The biosensor 100 then correlates the detected characteristics of the underlying tissue with known or predetermined characteristics of underlying tissue (e.g. measured from an abdominal area, wrist, forearm, leg, etc.) to determine its positioning. Information of amount and types of movement from the activity monitoring circuit 114 may be used as well in the determination of position.

In response to the determined position and/or detected characteristics of the underlying tissue, the operation of the biosensor 100 is adjusted at 2114. For example, the biosensor 100 may adjust operation of the PPG circuit 110. The article, "Optical Properties of Biological Tissues: A Review," by Steven L. Jacques, Phys. Med. Biol. 58 (2013), which is hereby incorporated by reference herein, describes wavelength-dependent behavior of scattering and absorption of different tissues. The PPG circuit 110 may adjust a frequency or wavelength in detection of a concentration level of a substance based on the underlying tissue. The PPG circuit 110 may adjust an absorption coefficient when determining a concentration level of a substance based on Beer-Lambert principles due to the characteristics of the underlying tissue. Other adjustments may also be implemented depending on predetermined or measured characteristics of the underlying tissue.

Adjustments to the activity monitoring circuit 114 may need to be made depending on positioning as well. For example, the type and level of movement detected when positioned on a wrist of a patient may vary from the type and level of movement when positioned on an abdominal area of the patient. In another aspect, the biosensor 100 may adjust measurements from the temperature sensor 112 depending on placement of the patient, e.g. the sensor array measurements may vary from a wrist or forehead.

The biosensor 100 is thus configured to obtain position information and perform adjustments to its operation in response to the position information.

Embodiment—Diabetic Parameter Measurements

Clinical data obtained using the biosensor 100 is now described herein. The biosensor 100 was used to monitor concentration levels or indicators of one or more substances in the blood flow of the patient in the clinical trials over a measurement time period. For example, the biosensor 100 was used in the clinical trials to non-invasively detect diabetic parameters, such as insulin response over time, nitric oxide (NO) levels, glucose levels, and predict diabetic risk or diabetic precursors, in pulsatile arterial blood flow. The biosensor 100 was also used to detect blood alcohol levels in pulsatile arterial blood flow. The biosensor 100 was also used to detect digestive parameters, such as digestion phase 1 and 2 responses. The biosensor 100 also detected heart rate and blood oxygen saturation levels in the clinical trials.

Figure 22:
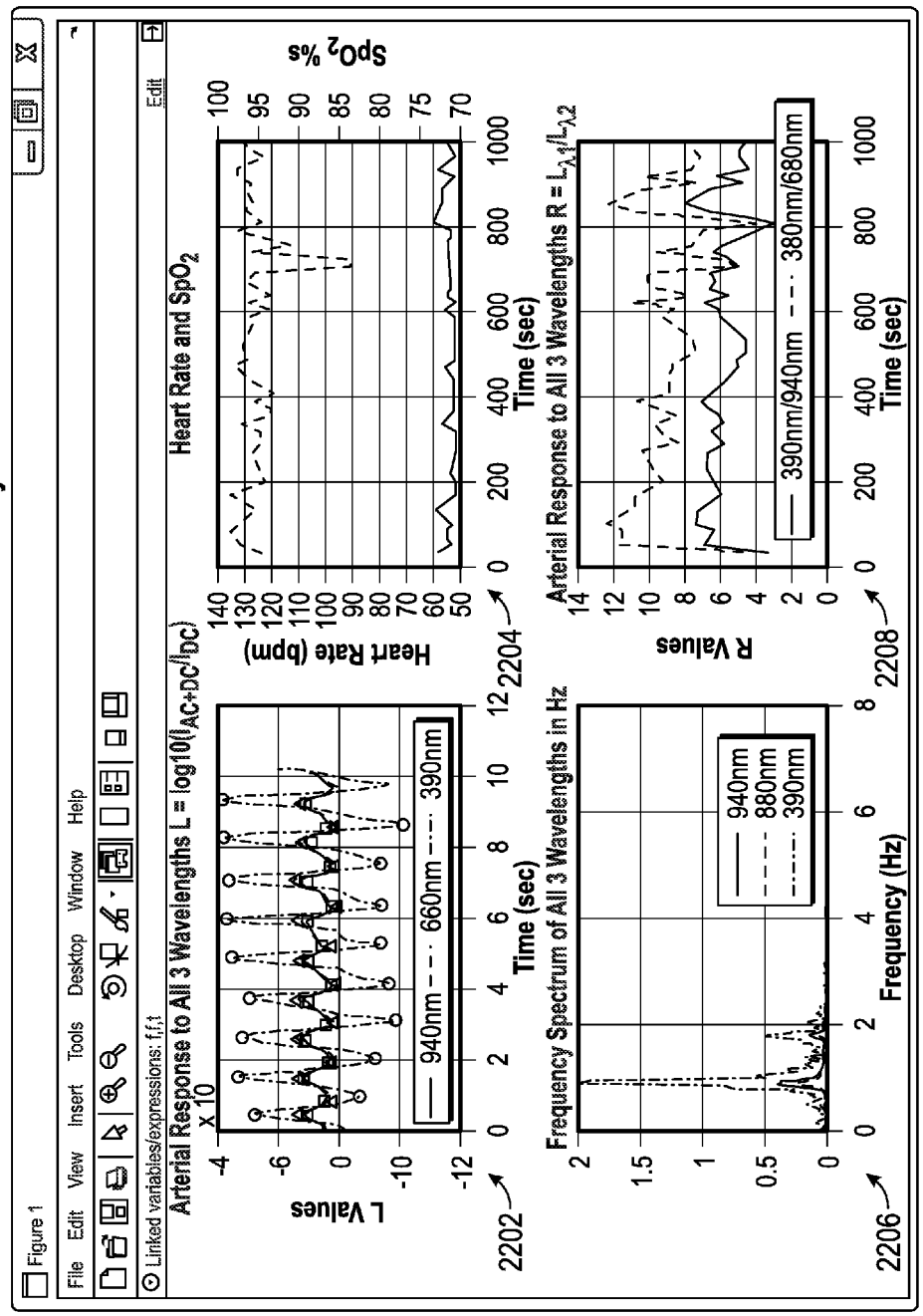
FIG. 22 illustrates a schematic drawing of an exemplary embodiment of results of clinical data obtained using an embodiment of the biosensor from a first patient.

FIG. 22 illustrates a schematic drawing of an exemplary embodiment of results of clinical data 2200 obtained using an embodiment of the biosensor 100 from a first patient. This first patient is a 42 year old female with no known diagnosis of diabetes or other conditions. A biosensor 100 is placed on at least one finger of the first patient and the spectral response is measured over the least three wavelengths at 390 nm, 660 nm and 940 nm (and also in range of 1 nm to 50 nm). The graph 2006 illustrates the spectral response or frequency spectrum data obtained for the three wavelengths. The spectral response in graph 2206 shows the frequency versus the relative intensity measured by the biosensor 100. The graph 2202 illustrates the L value obtained from the spectral responses for each of the three wavelengths obtained, e.g., from the spectral response data shown in graph 2206. The L value obtained for the three wavelengths is a measured response from the pulsating arterial blood flow in the patient.

The graph 2208 illustrates the calculated Ratio R for $R_1=L_{390\ nm}/L_{940\ nm}$ and $R_2=L_{390\ nm}/L_{660\ nm}$. In one aspect, based on unexpected results from clinical trials, it was determined that a ratio R value obtained at approximately $L_{\lambda1}=390$ nm and $L_{\lambda2}=940$ nm is useful as a predictor or indicator of diabetic risk or diabetes. For example, during experimental clinical trials, spectral responses were obtained during a measurement period over a 1-2 minute time period for wavelengths of 390 nm and 940 nm (and also in ranges of 1 nm to 50 nm including these wavelengths). An R value was obtained based on the spectral responses. From the unexpected results of the clinical trials, an R value obtained during a period of fasting, e.g. prior to ingestion of food or liquids, of less than 1 (e.g., approximately 0.5) indicated that a person has diabetes or early onset of diabetes. An R value of 2 or above indicated that a person has a lower risk of a diabetes diagnosis. An R value in the 5-6 range indicated no current risk of diabetes. For example, as shown in graph 2208, the R value obtained for $L_{\lambda1}=390$ nm and $L_{\lambda2}=940$ nm has an average value greater than 5 in this first patient without a diabetes diagnosis.

In particular, in unexpected results, it is believed that nitric oxide NO levels in the arterial blood flow is being measured at least in part by the biosensor 100 using the spectral response for the wavelength 390 nm (and 1 nm-50 nm range around 390 nm). The spectral response is responsive to nitric oxide (NO) concentration levels in the blood. As such, the $L_{390\ nm}$ values may be used to determine nitric oxide (NO) concentration levels in the pulsating blood flow.

In addition, insulin in the blood generates NO as it penetrates blood vessel walls. The NO is released as a gas before attaching to one or more hemoglobin type molecules. Since at least part of the NO gas concentration is in a gaseous form in the arterial blood flow, the NO in the gaseous form will dissipate prior to measurement from in vitro blood samples. As such, the complete NO concentration levels may not be measured using in vitro blood samples, e.g. from a finger prick. Thus, the biosensor 100 measurements, e.g. using the spectral response and calculated L values at 390 nm, are the first time NO levels in arterial blood flow have been measured in vivo. These unexpected results of measuring nitric oxide NO concentration levels in pulsating arterial blood flow are obtained non-invasively and continuously over a measurement period using the biosensor 100.

From the clinical trials performed, it has been determined that the measured NO levels are an indication of insulin response and blood glucose concentration levels in the blood. The R value derived from $L_{390\ nm}/L_{940\ nm}$ may thus be used as an indicator of insulin response and diabetic risk as well as vascular health. These unexpected results have advantages in early detection of diabetic risk and easier, non-invasive monitoring of insulin resistance and blood glucose levels. The biosensor 100 may display the R value or an analysis of the diabetic risk based on the R value. In one aspect, the biosensor 100 may display, no diabetic risk based on R values of 5 or greater. In another aspect, the biosensor 100 may display, low diabetic risk based on R values of 2-5. In another aspect, the biosensor 100 may display, high diabetic risk based on an R values of 1-2. In another aspect, the biosensor 100 may display, diabetic condition detected based on an R value less than one.

Figure 23:
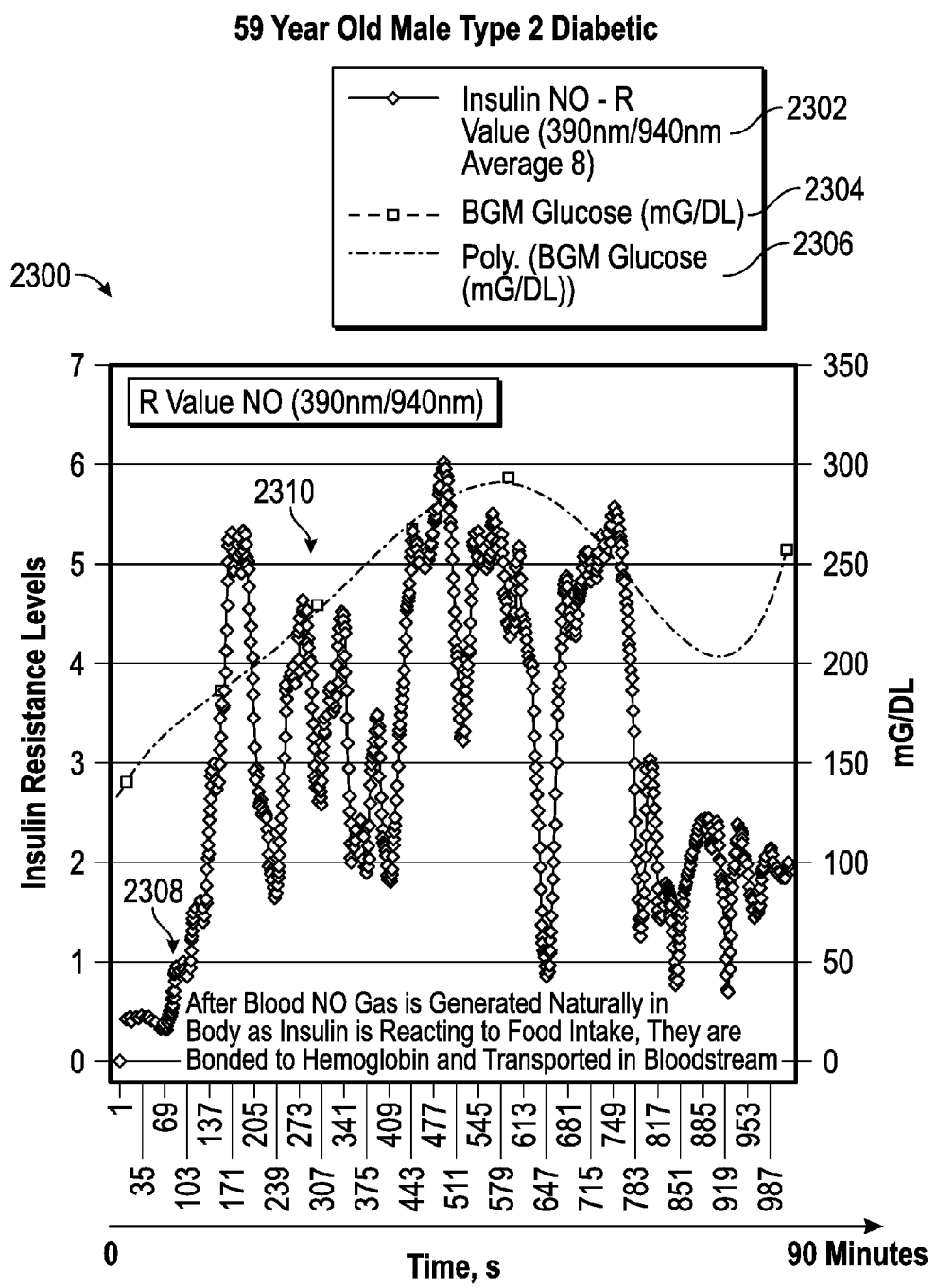
FIG. 23 illustrates a schematic drawing of another exemplary embodiment of results of clinical data obtained using an embodiment of the biosensor from a second patient.

FIG. 23 illustrates a schematic drawing of another exemplary embodiment of results of clinical data 2300 obtained using an embodiment of the biosensor 100 from a second patient. The second patient is a 59 year old male with a known diagnosis of Type 2 diabetes. At predetermined time periods of about 15 minutes, blood glucose level (BGL) was measured using a known method of a blood glucose meter (BGM) using blood from finger pricks. The BGM glucose measurements 2304 are plotted. The plotted measurements were interpolated to generate a polynomial 2306 showing the approximate BGM glucose measurements over time in mG/DL units. The biosensor 100 obtained measurements over the same time period to derive the Ratio R for approximately $L_{390\ nm}/L_{940\ nm}$ 2302, as shown on the graph as well.

In this clinical trial, the base insulin resistance factor 2308 measured prior to eating has a low baseline value of about 0.5 indicating a diabetic condition. In unexpected results, the base insulin resistance factor or R value for $L_{390\ nm}/L_{940\ nm}$ of less than 1 (in an R value range of 0-8) thus seems to indicate a diabetic condition from the clinical trial results. After consumption of a high sugar substance, insulin response 2310 is seen after about 7 minutes. The blood glucose levels may be obtained from the R values using the graph 2300 or a similar calibration table that correlates the R value with known BGL measurements for the patient. The calibration table may be generated for a specific patient or may be generated from a sample of a general population. It is determined that the R values should correlate to similar BGL measurements across a general population. Thus, the calibration table may be generated from testing of a sample of a general population.

From the unexpected results of the clinical trials, an R value of less than 1 (in an R value range of 0-8) indicated that a person has diabetes or early onset of diabetes. An R value of 5 (in an R value range of 0-8) or above indicated that a person has no diabetic condition. For example, as shown in graph 2208, the base insulin resistance factor measured using an R value of approximately $L_{390\ nm}/L_{940\ nm}$ has generally an average value greater than 5 in the first patient without a diabetes diagnosis. The base insulin resistance factor measured using an R value of approximately $L_{390\ nm}/L_{940\ nm}$ was generally an average value less than 1 (in an R value range from 0-8) in the other patients with a diabetes diagnosis of either Type 1 or Type II. The base insulin resistance factor measured using an R value in the 1-2 (in an R value range from 0-8) range indicated a high risk of diabetes and need for further testing.

It seems that the $L_{390\ nm}$ is measuring NO levels in the arterial blood flow. As insulin is generated in the body, it reacts with blood vessels to generate NO gas. The NO gas bonds to hemoglobin and is transported in the blood stream. The NO is thus a good indicator of a base insulin resistance factor after fasting and an insulin response after caloric intake.

From the clinical trials, it seems that the NO levels are reflected in the R values obtained from $L_{390}/L_{940}$. Based on the clinical trials and R values obtained in the clinical trials, it is determined that a base insulin resistance factor of less than 1 corresponds to an NO concentration level of at least less than 25% of average NO levels. For example, average NO levels are determined by sampling a general population of persons without diabetes or other health conditions affecting NO levels. From the clinical trials, an R value correlating to a base insulin factor of less than 1 indicates that the NO levels are in a range of 25% to 50% less than average NO levels. After fasting, a person with a diabetic condition will have low NO concentration levels that are at least 25% less than average NO levels due to the low level of insulin in the blood. Thus, an NO concentration level of at least less than 25% of normal ranges of NO concentration levels indicates a diabetic condition (e.g., the NO levels corresponding to R value less than 1 in this clinical trial). Thus, a base insulin resistance factor of less than 1 correlates to at least less than 25% of average NO levels of a sample population and indicates a diabetic condition.

Based on the clinical trials and R values obtained in the clinical trials, it is determined that a base insulin resistance factor in the range of 2-8 corresponds to average NO concentration levels. Thus, a base insulin resistance factor (e.g. in the range of 2-8) correlates to an average NO level of a sample population and little to no diabetic risk.

Based on these unexpected results, in one aspect, the biosensor 100 may display or transmit, e.g. to a user device or monitoring station, or otherwise output an indicator of the diabetic risk of a patient based on the R value. For example, the biosensor 100 may output no diabetic risk based on an obtained R value for a patient of 5 or greater. In another aspect, the biosensor 100 may output low diabetic risk based on an obtained R value of 2-5. In another aspect, the biosensor 100 may output high diabetic risk based on an obtained R values of 1-2. In another aspect, the bio sensor 100 may output diabetic condition detected based on an R value less than one. In the clinical trials herein, the R value was in a range of 0-8. Other ranges, weights or functions derived using the R value described herein may be implemented that changes the numerical value of the R values described herein or the range of the R values described herein. In general, from the results obtained herein, an R value corresponding to at least the lower 10% of the R value range indicates a diabetic condition, an R value in the lower 10% to 25% of the R value range indicates a high risk of diabetes, an R value in the 25% to 60% range indicates a low risk of diabetes, and an R value greater than 60% indicates no diabetic condition.

The R value of $L_{390\ nm}/L_{940\ nm}$ may be non-invasively and quickly and easily obtained using the biosensor 100 in a physician's office or other clinical setting or at home. In one aspect, the R value may be used to determine whether further testing for diabetes needs to be performed. For example, upon detection of a low R value of less than 1, a clinician may then determine to perform further testing and monitoring, e.g. using glucose ingestion tests over a longer period of time or using the biosensor 100 over a longer period of time or other type of testing.

Embodiment—Blood Alcohol Level Measurements

Figure 24:
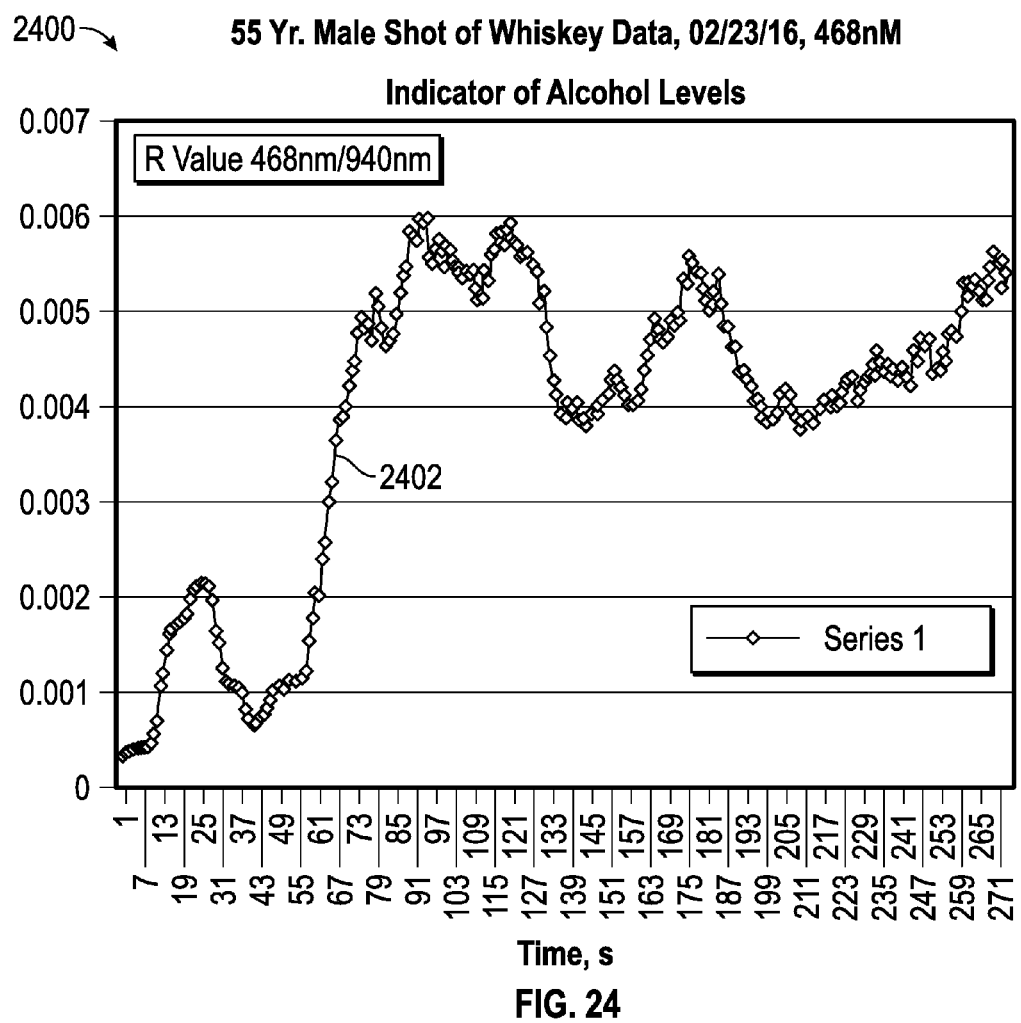
FIG. 24 illustrates a schematic drawing of another exemplary embodiment of results of clinical data obtained using an embodiment of the biosensor from a third patient.

FIG. 24 illustrates a schematic drawing of another exemplary embodiment of results of clinical data 2400 obtained using an embodiment of the biosensor 100 from a third patient. In this trial, the third patient was a 55 year old male that ingested a shot of whiskey at approximately 7 seconds. The biosensor 100 was used to measure an indicator of blood alcohol levels over a measurement period of approximately 271 seconds using a wavelength of approximately 468 nm. The graph illustrates the values obtained for ratio $R=L_{468\ nm}/L_{940\ nm}$ 2802 over the measurement period. The biosensor 100 was able to detect the increase in the blood alcohol levels over the measurement period. The ratio R values 2802 may be correlated with blood alcohol levels using a table or graph that associates the R values 2402 with blood alcohol levels. For example, the table or graph may be obtained through blood alcohol levels measured from blood drawn at preset intervals (such as every 1-5 minutes) during a measurement period (such as 1-5 hours) and interpolating the resulting measurements. The interpolated measurements are then associated with the measured ratio R values 2402 over the same measurement period. In general, the ratio R values 2402 are consistent with an approximate measured blood alcohol level in subsequent clinical trials for a patient. The calibration of measured blood alcohol levels to ratio R values 2402 may thus only be performed once for a patient. In another aspect, the calibration table may be generated using testing of a sample of a general population. It is determined that the R values should correlate to similar BAL measurements across a general population. Thus, the calibration table may be generated from testing of a sample of a general population.

In unexpected results, concentration levels of a liver enzyme called cytochrome P450 Oxidase (P450) that is generated in the presence of alcohol may be measured by the biosensor 100. The spectral response around the wavelength at approximately 468 nm seems to track the concentration levels of the liver enzyme P450. The liver enzyme is generated to react with various substances and may be generated in response to alcohol levels. Thus, the measurement of the spectral response for the wavelength at approximately 468 nm may indicate blood alcohol levels and/or concentration levels of P450.

Embodiment—Digestive Stage and Caloric Intake Measurements

Figure 25:
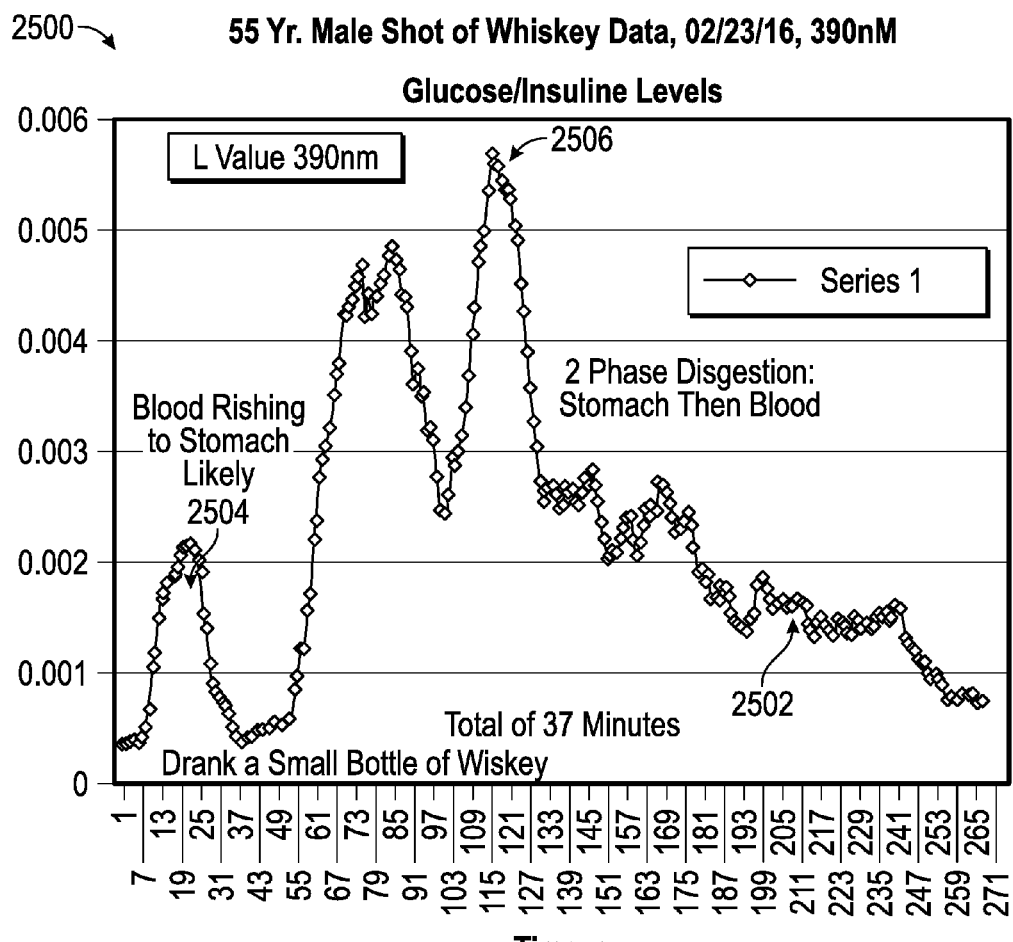
FIG. 25 illustrates a schematic drawing of another exemplary embodiment of results of clinical data obtained using the biosensor from a fourth patient.

FIG. 25 illustrates a schematic drawing of another exemplary embodiment of results of clinical data 2500 obtained using the biosensor 100 from a fourth patient. In this trial, the fourth patient ingested whiskey at approximately 13 seconds. The biosensor 100 was used to measure the digestive stages over a measurement period of approximately 37 minutes using a wavelength of approximately 390 nm to track the blood glucose levels. The graph illustrates the values for $L_{390\ nm}$ 2502 obtained over the measurement period. The biosensor 100 was able to detect the digestive stage 1 2504 and digestive stage 2 2506 based on the obtained values for $L_{390\ nm}$. The first digestive stage 1 2504 is indicated by an initial spike around 20 seconds as blood rushes to the stomach to aid in digestion. The second digestive stage 2 is indicated by a later, more prolonged increase in blood glucose levels between 60 and 180 seconds.

Based on the insulin response and BGL measurements, a calibration of caloric intake may be performed for a patient. For example, known caloric intakes may be correlated with insulin response in phase 1 and phase 2 digestions measured using values for $L_{390\ nm}$ 2502. In another aspect, the calibration table may be generated using testing of a sample of a general population. It is determined that the R values using $L_{390}$. 2502 should correlate to similar caloric intake measurements across a general population. Thus, the calibration table may be generated from testing of a sample of a general population.

Embodiment—Liver Enzyme Measurements

In unexpected results, concentration levels of a liver enzyme called cytochrome P450 Oxidase (P450) 2600 was measured by the biosensor 100. In one aspect, spectral response around a wavelength at approximately 468 nm was used by the biosensor 100 to obtain L values that tracked the concentration levels of the liver enzyme P450 2600. The liver enzyme is generated to react with various substances 2602 and may be generated in response to alcohol levels. Thus, the measurement of the spectral response for the wavelength at approximately 468 nm may indicate blood alcohol levels and/or concentration levels of P450 2600.

Embodiment—Measurements of Other Substances

Using similar principles described herein, the biosensor 100 may measure concentration levels or indicators of other substances in pulsating blood flow. For example, using the process 1500 described with respect to FIG. 15, absorption coefficients for one or more frequencies that have an intensity level responsive to concentration level of substance may be determined. The biosensor 100 may then detect the substance at the determined one or more frequencies as described herein and determine the concentration levels using the Beer-Lambert principles and the absorption coefficients. The L values and R values may be calculated based on the obtained spectral response. In one aspect, the biosensor 100 may detect various electrolyte concentration levels or blood analyte levels, such as bilirubin (using $L_{460\ nm}$) and iron (using $L_{510\ nm}$, $L_{651\ nm}$, $L_{300\ nm}$) and potassium (using $L_{550\ nm}$).

In another aspect, the biosensor 100 may detect sodium chloride NACL (using $L_{450\ nm}$) concentration levels in the arterial blood flow and determine dehydration level. The biosensor 100 may then output a determination of level of dehydration based on the detected NACL concentration levels.

In yet another aspect, the biosensor 100 may be configured to detect proteins or abnormal cells or other elements or compounds associated with cancer. The biosensor 100 may measure concentration levels or indicators of other substances in pulsating blood flow using similar principles described herein.

For example, the value $L_{\lambda 1}$ is determined from a spectral response of a wavelength with a high absorption coefficient for the targeted substance. The value $L_{\lambda 2}$ is determined from a spectral response of the wavelength with a low absorption coefficient for the targeted substance. The ratio $R_{\lambda 1,\lambda 2}$ is determined from the value $L_{\lambda 1}$ and the value $L_{\lambda 2}$. A calibration table may be generated using testing of a sample of a general population that correlates values of the ratio $R_{\lambda 1,\lambda 2}$ to concentration levels of the target substance. Then the concentration level of the targeted substance may be determined using the calibration table and the measured values for the ratio $R_{\lambda 1,\lambda 2}$.

Embodiment—White Blood Cell Levels and Detection of Infection

The biosensor 100 may detect white blood cell levels and determine a presence of an infection. For example, the biosensor 100 may detect the various types of white blood cells based on the spectral response of the wavelengths, e.g. using one or more wavelengths shown in Table 1 below.

TABLE 1

Detection of White Blood Cells

| White Blood Cell Type | Diameter | Color | Spectral Absorption Wavelengths |
|---|---|---|---|
| Neutrophil | 10-12 um | Pink - Red, Blue, White | Red - 660 nm<br>Blue - 470 nm<br>Green - 580 nm |
| Eosinophil | 10-12 um | Pink Orange | 660 nm, 470 nm, 580 nm<br>600 nm |
| Basophil | 12-15 um | Blue | 470 nm |
| Lymphocyte | 7-15 um | | 633 nm |
| Monocyte | 15-30 um | | 580 nm |

The biosensor 100 may detect a color or color change of the blood due to an increase or decrease in white blood cells using one or more wavelengths described in Table 1. Based on the detected color or color change of the blood, the biosensor 100 may output an alert to a presence of an infection. For example, the biosensor 100 monitors the color of the blood. When it detects a color change indicating an increase in white blood cells, the biosensor determines whether this color change meets a predetermined threshold indicating a presence of an infection. The predetermined threshold may include a color scale and/or length of time of color change. When the color change reaches the predetermined threshold, the biosensor 100 transmits or displays an alert to indicate a presence of an infection.

In another aspect, the biosensor 100 may detect white blood cells from spectral responses at one or more wavelengths. Due to the larger size of the white blood cells from red blood cells, the presence of white blood cells in the blood affects the spectral width and shape of a spectral response.

Figure 26:
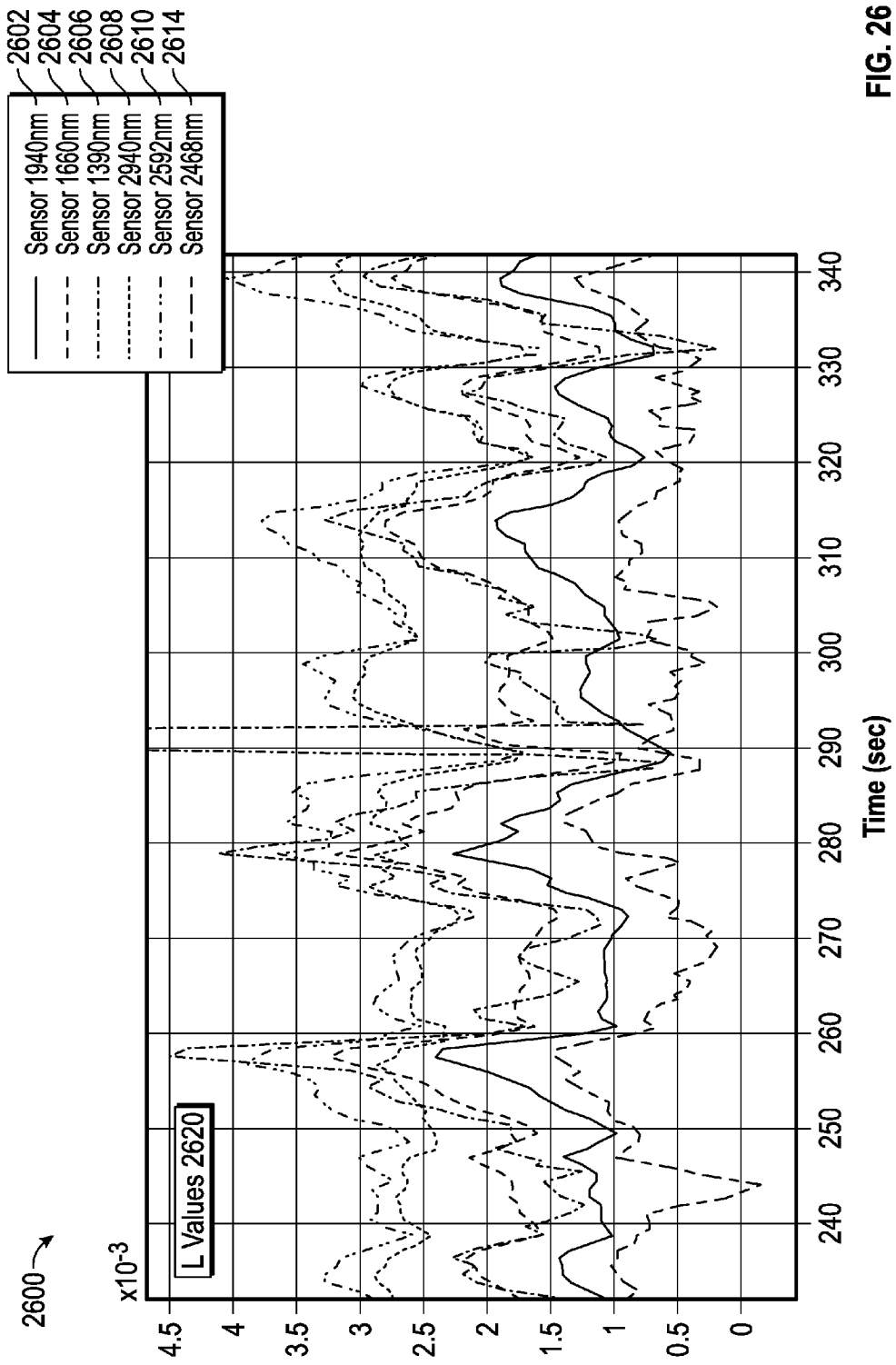
FIG. 26 illustrates an exemplary graph of spectral responses of a plurality of wavelengths from clinical data using the biosensor

FIG. 26 illustrates an exemplary graph 2600 of spectral responses of a plurality of wavelengths from clinical data using the biosensor 100. In this embodiment, the spectral response of a plurality of wavelengths was measured using the biosensor 100 over a measurement period of almost 600 seconds or approximately 10 minutes. The graph illustrates the L values calculated from the spectral response for a first wavelength 1402 of approximately 940 nm, the spectral response for a second wavelength 1404 of approximately 660 nm and the spectral response for a third wavelength 1406 of approximately 390 nm obtained from a first biosensor 100 measuring reflected light from a first fingertip of a patient. The graph further illustrates the spectral response for a fourth wavelength 1410 of approximately 592 nm and a fifth wavelength 1412 of approximately 468 nm and the spectral response 1408 again at 940 nm obtained from a second biosensor measuring reflected light from a second fingertip of a patient. The spectral responses are temporally aligned using the systolic and diastolic points. Though two biosensors were used to obtain the spectral responses in this clinical trial, a single biosensor 100 may also be configured to obtain the spectral responses of the plurality of wavelengths.

Due to the size of the white blood cells, the presence of white blood cells in the blood affects the spectral width and shape of a spectral response at one or more wavelengths. In one aspect, from L values 2620 shown for the spectral response at 660 nm 2604, the width and shape of the spectral response is affected by the presence of white blood cells. For example, the width and shape of L660 nm between 250 and 270 seconds has a different shape and width of L66 nm between 300 and 320 seconds in the graph 2600. The differences in the width and shape of the spectral response may be used to determine a concentration level of white blood cells or change in concentration level of white blood cells in the blood.

For example, neutrophil levels increase in the presence of an infection. The neutrophil particles have a different color and size from red blood cells. The biosensor 100 may determine an increase in concentration of neutrophil in response to a change in color of the blood or change in the pattern of the spectral response (L value and/or R value) due to change in size of particles in the blood or a combination of both a change in color and change in a pattern of the spectral response (L value and/or R value).

Figure 27:
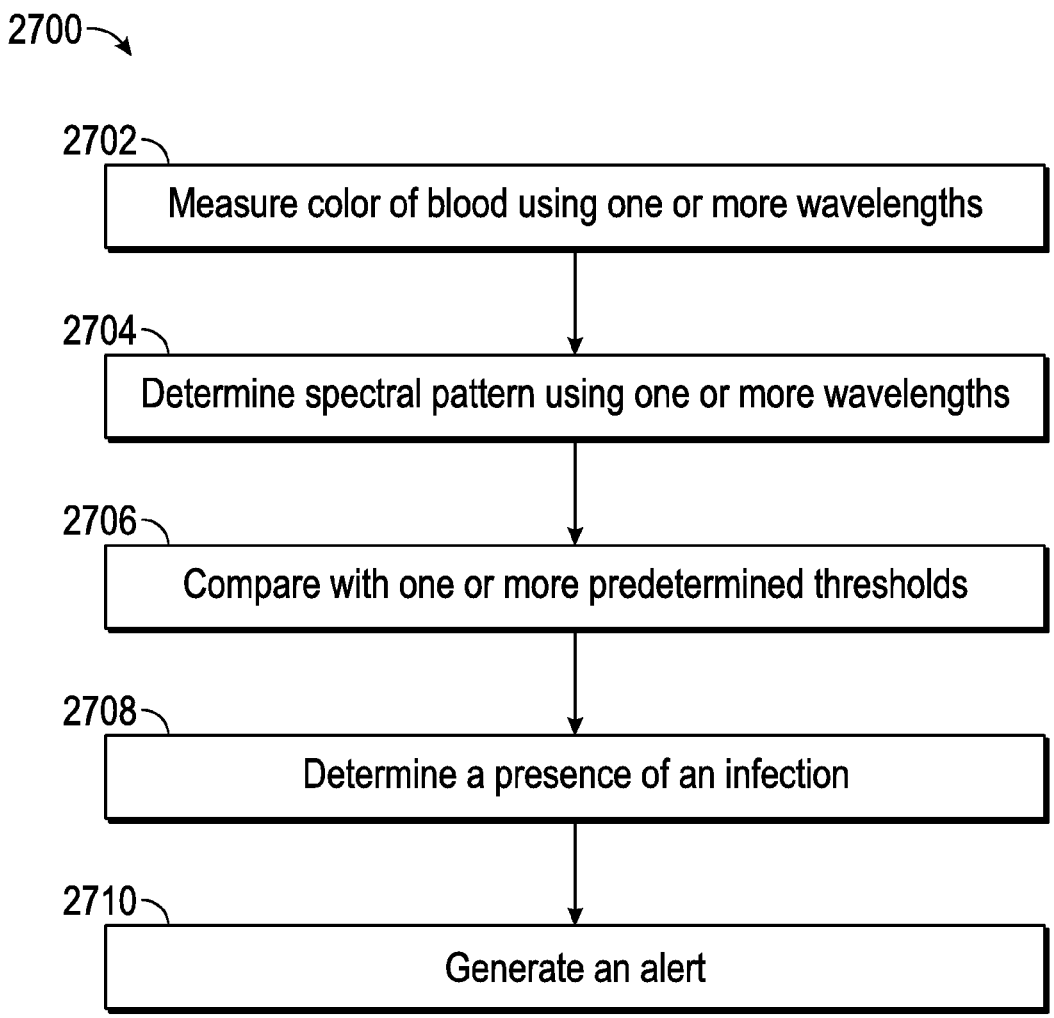
FIG. 27 illustrates a logical flow diagram of an embodiment of a method to determine a presence of an infection by the biosensor.

FIG. 27 illustrates a logical flow diagram of an embodiment of a method 2700 to determine a presence of an infection by the biosensor 100. The biosensor 100 measures a color or color change of the blood using one or more wavelengths at 2702. The biosensor 100 may also determine a spectral pattern (e.g. from L values or R values) using one or more wavelengths. The biosensor 100 is configured to compare the color and/or spectral pattern to one or more predetermined thresholds indicating a presence of an infection at 2704. The one or more predetermined thresholds may include a color scale, spectral patterns and/or length of time of color change or level of white blood cells detected. For example, the biosensor 100 may correlate the determined spectral patterns with one or more known spectral patterns indicating presence of white blood cells. In another example, the biosensor 100 may compare the measured color hue, shade or intensity of the blood with known color hues, shades, or intensities indicating a presence of an infection. When the biosensor 100 detects the biosensor data meets the one or more predetermined thresholds, the biosensor 100 determines a presence of infection at 2708. The biosensor 100 is configured to transmit or display an alert to indicate a presence of the infection at 2710.

Embodiment—Detection of Sleep Apnea

In another aspect, the biosensor 100 may detect sleep apnea. The biosensor 100 is configured to determine periods of sleep of the patient. The determination may be based on input from the activity monitoring circuit 114, measured respiration rates, heart rate, etc. The biosensor 100 monitors and tracks the oxygen saturation levels $SpO_2$ during the periods of sleep. The biosensor 100 may compare the measured pattern of the oxygen saturation levels during sleep with known patterns associated with sleep apnea. Based on this comparison, the biosensor 100 may determine a sleep apnea diagnosis or a high or low risk of sleep apnea for a patient.

Embodiment—Functions Through Health Care Management Chain

Figure 28:
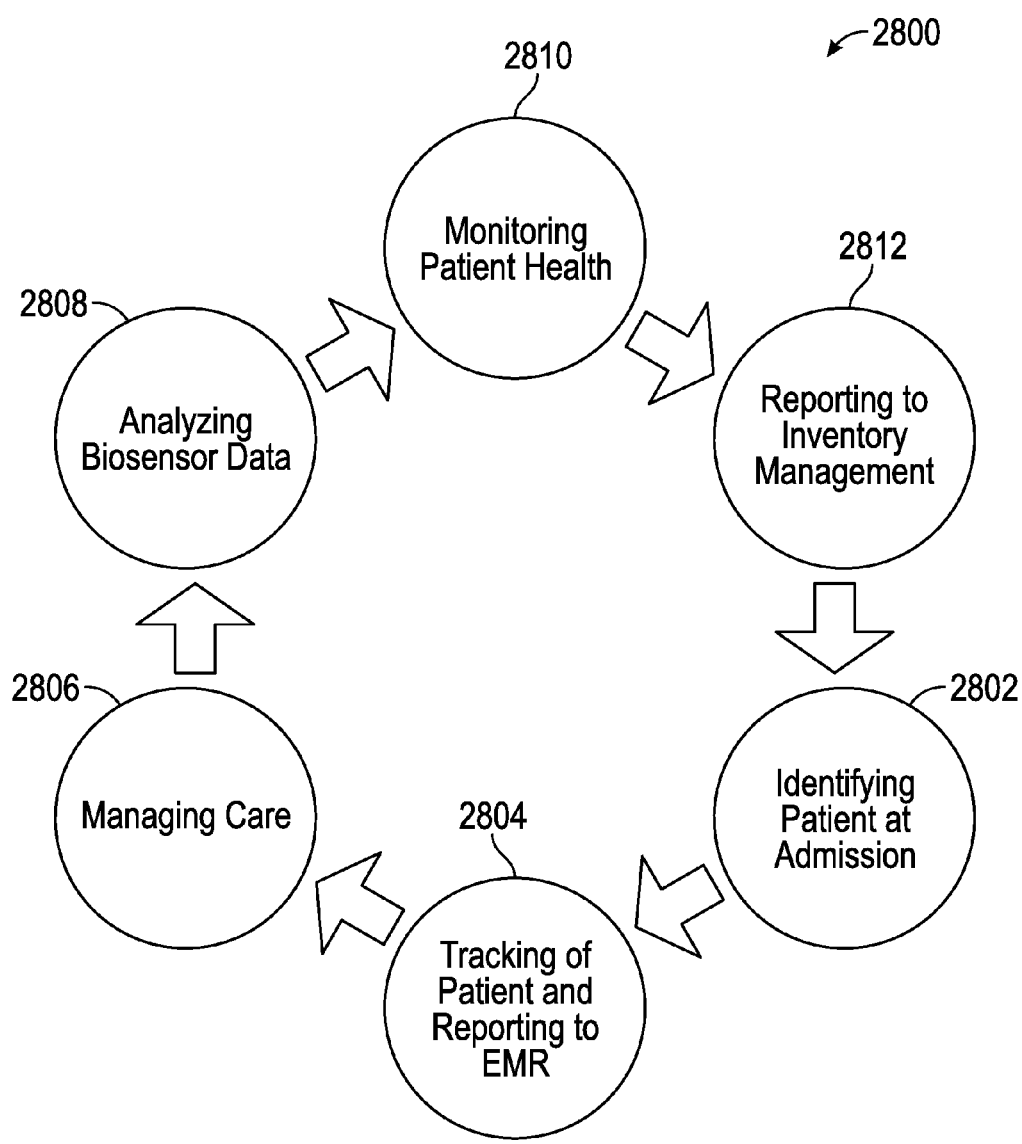
FIG. 28 illustrates a schematic block diagram of an embodiment of a method for using the biosensor throughout the health care management of a patient.

FIG. 28 illustrates a schematic block diagram of an embodiment of a method 2800 for using the biosensor 100 throughout the health care management of a patient. The unique patient identification and biosensor data obtained by the biosensor 100 may be used in one or more applications or systems in the health care management of a patient. A plurality of these functions may be performed concurrently as well as other functions and processes described herein.

At 2802, prior to or at admission, the biosensor 100 is activated for a patient and programmed with a unique patient identification for identifying the patient. The unique patient identification number is programmed into the memory of the biosensor 100 and is associated with the patient and the EMR of the patient. For example, the biosensor 100 may be assigned to a patient upon entry to an emergency room at check-in. The biosensor 100 may begin tracking the patient's vitals and other biosensor data prior to a first assessment by a healthcare provider. Thus, a patient's condition may be monitored and alerts generated while a patient is waiting for assessment by physician or other health care provider in an emergency room. The physician or other health care provider will then have a record of the patient's vitals and other biosensor data obtained by the biosensor 100 at the assessment.

At 2804, the biosensor 100 wirelessly communicates the patient identification with biosensor data to one or more devices for tracking and monitoring of the patient and storing the biosensor data to the patient's EMR. The biosensor 100 may be used to identify the patient without a need for a scanner. The biosensor 100 may also be used for tracking a location of patient in the health care facility based on the wireless communications to one or more local devices. The biosensor 100 may be used to track wait times in an emergency room, time and length of procedures, medication times and dosages, procedures performed, etc.

At 2806, the biosensor 100 may be used for managing the care of the patient. For example, the biosensor data 100 may be used to schedule and/or store physician consultations, physician diagnosis, projected discharge dates, recommended discharge orders, treatment options, etc.

At 2810, the biosensor 100 may be used for analyzing the biosensor data. In one aspect, the biosensor 100 or other device may analyze the biosensor data to determine efficacy of treatment. For example, the biosensor data may be analyzed to determine whether the condition of the patient improved over the course of treatment or to determine the treatments with more positive or negative results. The biosensor data may be analyzed to determine genetic predispositions—or conditions. The biosensor data may be analyzed to determine diagnosis of conditions and treatment options.

At 2810, the biosensor 100 is configured for monitoring of patient health as described herein. The biosensor 100 is configured to monitor patient's vitals, determine concentration of one or more substances in the blood, and perform other monitoring operations described. The biosensor data obtained by the biosensor 100 is transmitted with the unique patient identification for monitoring by a remote monitoring station or storage in the patient EMR. The patient identification stored by the biosensor 100 is wirelessly communicated to one or more local devices to record administration of medication, performance of procedures, etc. Thus, the biosensor 100 continuously and non-invasively monitors the health of the patient. The biosensor 100 may replace the need to measure the patient's vitals with a vitals cart and for drawing blood to determine concentrations of substances in the blood. The biosensor 100 also replaces scanning of the barcode on an arm band to identify a patient. The biosensor 100 also replaces the need to manually input vitals by a health care provider.

At 2812, the biosensor 100 may also transmit wirelessly or report information to an inventory management system. For example, when a medication is provided to a patient, this information of the medication and dosage may be reported to the inventory management system. In another example, when medical supplies are provided to a patient, the medical supplies may include an RFID tag or other identifier that is sensed or obtained by the biosensor 100. The biosensor 100 transmits the identification of the medical supply and the patient identification to the inventory management system. The inventory management system is then able to adjust the inventory of the medical supply. The biosensor 100 may thus report information on usage of medication or other medical supplies for a patient to the inventory management system. Similar information may be reported to a billing system for invoicing to the patient.

The biosensor 100 and health care band 50 provide for continuous monitoring of a patient's vitals without need for additional instruments, manual intervention or disturbing a patient's sleep. The biosensor 100 may also be used to perform a blood panel analysis based on in vivo arterial blood flow without need for invasive blood samples from a patient. The biosensor 100 wirelessly communicates the biosensor data and associated patient identification for monitoring and storage in the patient's EMR. Thus, a separate scanner for identifying the patient and vitals cart or other additional instrumentation is not always needed to monitor the health of the patient.

Though the above description includes details with respect to pulsating arterial blood flow, the biosensor 100 may use similar techniques described herein for pulsating venous blood flow. The biosensor 100 is positioned on skin tissue over veins, such as on the wrist, and spectral responses obtained from light reflected by or transmitted through the pulsating venous blood flow.

One or more embodiments have been described herein for the non-invasive and continuous biosensor 100. Due to its compact form factor, the biosensor 100 may be configured for measurements on various skin surfaces of a patient, including on a forehead, arm, wrist, abdominal area, chest, leg, ear lobe, finger, toe, ear canal, etc. The biosensor includes one or more sensors for detecting biosensor data, such as a patient's vitals, activity levels, or concentrations of substances in the blood flow of the patient. In particular, the PPG sensor is configured to monitor concentration levels or indicators of one or more substances in the blood flow of the patient. In one aspect, the PPG sensor may non-invasively and continuously detect diabetic parameters, such as insulin resistance, insulin response over time, nitric oxide (NO) levels, glucose levels, and predict diabetic risk or diabetic precursors, in pulsatile arterial blood flow. In another aspect, the PPG sensor may measure vascular health using NO concentration levels. In another aspect, the PPG sensor may detect blood alcohol levels in pulsatile arterial blood flow. In another aspect, the PPG sensor may detect cytochrome P450 proteins or one or more other liver enzymes or proteins. In another aspect, the PPG sensor may detect digestive parameters, such as digestion phase 1 and 2 responses. The PPG sensor may detect various electrolyte concentration levels or blood analyte levels, such as bilirubin and sodium and potassium. For example, the PPG sensor may detect sodium NACL concentration levels in the arterial blood flow to determine dehydration. In yet another aspect, the PPG sensor may be configured to help diagnose cancer by detecting proteins or abnormal cells or other elements or compounds associated with cancer. In another aspect, the PPG sensor may detect white blood cell counts.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. §112(f) as a "means-plus-function" type element, unless the element is expressly recited using the phrase "means for" or, in the case of a method claim, the element is recited using the phrase "step for."

The invention claimed is:

1. A health care monitoring system, comprising:
a health care band configured for attachment to a patient;
a biosensor attached to the health care band, comprising:
 a memory configured to store a unique patient identification;
 a temperature sensor configured to obtain a temperature of the patient;
 a PPG circuit configured to emit light at a plurality of wavelengths directed at skin of the patient and obtain a plurality of spectral responses at each of the plurality of wavelengths of light reflected from the skin, including:
  obtaining a first spectral response around a first wavelength responsive to nitric oxide (NO) levels in arterial blood flow;
  obtaining a second spectral response around a second wavelength with a low absorption coefficient for nitric oxide (NO) in arterial blood flow;
 a processing circuit configured to:
  obtain an indicator of a concentration level of NO of the patient using the spectral responses at the plurality of wavelengths by:
   isolating a systolic point and a diastolic point in the first spectral response and obtain a value $L_{\lambda 1}$ using a ratio of the systolic point and the diastolic point in the first spectral response;
   isolating a systolic point and a diastolic point in the second spectral response and obtain a value $L_{\lambda 2}$ using a ratio of the systolic point and diastolic point in the second spectral response;
   obtaining a value $R_{\lambda 1, \lambda 2}$ from a ratio of the value $L_{\lambda 1}$ and the value $L_{\lambda 2}$, wherein the value $R_{\lambda 1, \lambda 2}$ is the indicator of the concentration level of NO of the patient;
  determine patient vitals using additional spectral responses, wherein the patient vitals include oxygen saturation levels; and
  obtain concentration levels of one or more additional substances in arterial blood flow using the spectral responses, including:
   obtaining a blood glucose concentration level of the patient from the indicator of the concentration level of NO of the value $R_{\lambda 1, \lambda 2}$ and a calibration table, wherein the calibration table correlates a plurality of the blood glucose concentration levels with a plurality of the values $R_{\lambda 1, \lambda 2}$; and
 a wireless transceiver configured to transmit the temperature, oxygen saturation levels, the blood glucose concentration level and the unique patient identification.

2. The health care monitoring system of claim 1, wherein the PPG circuit is further configured to:
obtain the value $L_{\lambda 1}$ using a first spectral response around a first wavelength responsive to a liver enzyme P450 in arterial blood flow; and
obtain the value $L_2$ using a second spectral response around a second wavelength with a low absorption coefficient for the liver enzyme P450 in arterial blood flow; and
obtain a liver enzyme value $R_{\lambda 1, \lambda 2}$ from the ratio of the value $L_{\lambda 1}$ from the first spectral response and the value $L_{\lambda 2}$ from the second spectral response, wherein the liver enzyme value $R_{\lambda 1, \lambda 2}$ is an indicator of the concentration level of the liver enzyme P450 in arterial blood flow.

3. The health care monitoring system of claim 2, wherein the processing circuit is configured to obtain concentration levels of one or more additional substances in arterial blood flow using the spectral responses by:
obtaining a concentration level of blood alcohol in the arterial blood flow using the liver enzyme value $R_{\lambda 1, \lambda 2}$ and a second calibration table, wherein the second calibration table correlates a plurality of blood alcohol concentration levels with a plurality of the liver enzyme values $R_{\lambda 1, \lambda 2}$.

4. The health care monitoring system of claim 1, wherein the PPG circuit is configured to:
obtain a value $L_{\lambda 1}$ using a first spectral response around a first wavelength responsive to a color of white blood cells in the arterial blood flow; and determine a presence of infection from the color of the white blood cells in the arterial blood flow.

5. The health care monitoring system of claim 1, wherein the PPG circuit is configured to:
obtain a first spectral response around a first wavelength responsive to white blood cells in the arterial blood flow; and
determine a spectral pattern using the first spectral response; and
determine a presence of infection from the spectral pattern.

6. The health care monitoring system of claim 1, wherein the biosensor further includes an attachment mechanism for detachment and attachment to the health care band.

7. The health care monitoring system of claim 1, wherein the health care band includes the unique patient identification encoded in a bar code.

8. The health care monitoring system of claim 1, wherein the wireless transceiver is configured to transmit the temperature, oxygen saturation levels, the concentration levels of the one or more additional substances and the unique patient identification to an EMR application server for recording in an electronic medical record associated with the unique patient identification.

9. The health care monitoring system of claim 1, wherein the PPG circuit includes a plurality of photodetectors configured in different physical positions and orientations and coupled in parallel to obtain the plurality of spectral responses at each of the plurality of wavelengths of light reflected from the skin.

10. The health care monitoring system of claim 1, wherein the concentration levels of the one or more additional substances includes two or more of: a blood alcohol level, a liver enzyme level, a cancer indicating protein, a sodium chloride level, a potassium level, a bilirubin level, and an iron level.

11. A biosensor configured for attachment to a patient, comprising:
a memory configured to store a unique patient identification;
a temperature sensor configured to obtain a temperature of the patient;
a PPG circuit configured for obtaining a concentration level of nitric oxide (NO) of the patient, wherein the PPG circuit is configured to:
generate at least a first spectral response for light reflected around a first wavelength from skin tissue of the patient, wherein the first wavelength is responsive to nitric oxide (NO) levels in arterial blood flow;
generate at least a second spectral response for light detected around a second wavelength reflected from the skin tissue of the patient, wherein the second wavelength has a low absorption coefficient for nitric oxide (NO) in arterial blood flow;
a processing circuit configured to:
process the first and second spectral responses at the first wavelength and the second wavelength;
obtain a glucose concentration level in arterial blood flow using the first and second spectral responses by:
isolating a systolic point and a diastolic point in the first spectral response and obtain a value $L_{\lambda 1}$ using a ratio of the systolic point and the diastolic point in the first spectral response;
isolating a systolic point and a diastolic point in the second spectral response and obtain a value $L_{\lambda 2}$ using a ratio of the systolic point and diastolic point in the second spectral response;
obtaining a value $R_{\lambda 1, \lambda 2}$ from a ratio of the value $L_{\lambda 1}$ and the value $L_{\lambda 2}$, wherein the value $R_{\lambda 1, \lambda 2}$ indicates a concentration level of NO of the patient; and
accessing a calibration table that includes a plurality of glucose concentration levels correlated with a plurality of concentration levels of NO; and
obtaining the glucose concentration level of the patient from the value $R_{\lambda 1, \lambda 2}$ of the patient and the calibration table; and
a wireless transceiver configured to transmit the temperature, glucose concentration level and the unique patient identification.

12. The biosensor of claim 11, wherein
the value $L_{\lambda 1}$ isolates the first spectral response due to pulsating arterial blood flow; and
wherein the value $L_{\lambda 2}$ isolates the second spectral response due to pulsating arterial blood flow.

13. The biosensor of claim 11, wherein wireless transceiver is configured to transmit the temperature, glucose concentration level and the unique patient identification to an EMR application server for recording in an electronic medical record associated with the unique patient identification.

14. The biosensor of claim 11, wherein the PPG circuit includes a plurality of photodetectors configured in different physical positions and orientations and coupled in parallel to obtain the plurality of spectral responses at each of the plurality of wavelengths of light reflected from the skin.

15. The biosensor of claim 11, wherein the PPG circuit is further configured to obtain a concentration level of one or more additional substances including two or more of: a blood alcohol level, a liver enzyme level, a cancer indicating protein, a sodium chloride level, a potassium level, a bilirubin level, an iron level and a white blood cell level.

16. The biosensor of claim 11, wherein the biosensor is configured for attachment to a patient on an arm, a wrist, a leg, a finger, a forehead, an earlobe or ear canal.

17. The biosensor of claim 11, wherein the biosensor is further configured to:
determine a position of the biosensor, wherein the position of the biosensor includes at least one area of a body of the patient; and
adjust operation of the PPG circuit in response to the position of the biosensor.

18. The biosensor of claim 17, wherein the processing circuit is configured to determine a position of the biosensor by:
obtaining a spectral response of underlying tissue from the PPG circuit;
detecting one or more characteristics of the underlying tissue from the spectral response;
correlating the detected one or more characteristics of the underlying tissue with predetermined characteristics of underlying tissue from a plurality of body areas, wherein the plurality of body parts include at least: an abdominal area, wrist, forearm, leg, earlobe or ear canal; and
determining the at least one area of the body of the patient on which the biosensor is located based on the correlation.

19. The biosensor of claim 18, wherein the biosensor is configured to adjust the operation of the PPG circuit in response to the position of the biosensor by:
adjusting a wavelength to transmit to obtain a spectral response to detect a concentration level of a substance in response to the underlying tissue.

20. The biosensor of claim 18, wherein the biosensor is configured to adjust the operation of the PPG circuit in response to the position of the biosensor by:
adjusting an absorption coefficient when determining a concentration level of a substance in response to the underlying tissue.

* * * * *

UNITED STATES PATENT AND TRADEMARK OFFICE
CERTIFICATE OF CORRECTION

| | | |
|---|---|---|
| PATENT NO. | : 9,642,538 B2 | Page 1 of 1 |
| APPLICATION NO. | : 15/275444 | |
| DATED | : May 9, 2017 | |
| INVENTOR(S) | : Robert Steven Newberry | |

It is certified that error appears in the above-identified patent and that said Letters Patent is hereby corrected as shown below:

On the Title Page

(63) Related U.S. Application Data reads:
Continuation-in-part of application No. 14/866,500, filed
on Sep. 25, 2015, and a continuation-in-part of
application No. 12/275,388 filed on Sep. 24, 2016.

(63) Related U.S. Application Data should read:
Continuation-in-part of application No. 14/866,500, filed
on Sep. 25, 2015, and a continuation-in-part of
application No. 15/275,388 filed on Sep. 24, 2016

Signed and Sealed this
First Day of August, 2017

Joseph Matal
*Performing the Functions and Duties of the
Under Secretary of Commerce for Intellectual Property and
Director of the United States Patent and Trademark Office*